(12) United States Patent
Savage et al.

(10) Patent No.: US 10,879,416 B2
(45) Date of Patent: Dec. 29, 2020

(54) METHODS OF SPERM CELL SENSING UTILIZING AN AVALANCHE PHOTODIODE AND CYTOMETER APPARATUS

(71) Applicant: ABS Global, Inc., DeForest, WI (US)

(72) Inventors: Frederick Savage, DeForest, WI (US); Glenn J. Szejna, Deforest, WI (US); Zheng Xia, DeForest, WI (US)

(73) Assignee: ABS Global, Inc., DeForest, WI (US)

(*) Notice: Subject to any disclaimer, the term of this patent is extended or adjusted under 35 U.S.C. 154(b) by 0 days.

(21) Appl. No.: 16/822,735

(22) Filed: Mar. 18, 2020

(65) Prior Publication Data

US 2020/0220038 A1 Jul. 9, 2020

Related U.S. Application Data

(60) Division of application No. 16/403,170, filed on May 3, 2019, now Pat. No. 10,763,387, which is a (Continued)

(51) Int. Cl.
*G01N 15/14* (2006.01)
*G01N 21/64* (2006.01)
(Continued)

(52) U.S. Cl.
CPC ..... *H01L 31/1075* (2013.01); *G01N 15/1404* (2013.01); *G01N 15/1425* (2013.01);
(Continued)

(58) Field of Classification Search
CPC .......... C12N 2529/10; C12N 5/061; G01J 2001/4453; G01N 15/1404; G01N 15/1425; G01N 15/1436; G01N 15/1459; G01N 2015/1006; G01N 21/00; G01N 21/645; H01L 31/024; H01L 31/1075
See application file for complete search history.

(56) References Cited

U.S. PATENT DOCUMENTS 5,953,690 A   9/1999  Lemon
10,333,018 B2  6/2019  Savage et al.
(Continued)

FOREIGN PATENT DOCUMENTS

WO    9800943 A1    1/1998

OTHER PUBLICATIONS

Premium Genetics (UK) Ltd, PCT/GB2018/052633 filed Sep. 14, 2018, "The International Search Report and the Written Opinion of the International Searching Authority, or the Declaration", 13 pages, dated Mar. 1, 2019.
(Continued)

*Primary Examiner* — Mark R Gaworecki
(74) *Attorney, Agent, or Firm* — McKee, Voorhees & Sease, PLC

(57) ABSTRACT

A cytometer includes an avalanche photodiode, a switching power supply, a filter, and voltage adjustment circuitry. The switching power supply includes a feedback loop. The filter is electrically connected between the switching power supply and the avalanche photodiode. The voltage adjustment circuitry adjusts a voltage on the feedback loop based at least in part on a voltage measured between the filter and the avalanche photodiode.

14 Claims, 19 Drawing Sheets

Related U.S. Application Data continuation of application No. 16/056,003, filed on Aug. 6, 2018, now Pat. No. 10,333,018, which is a continuation of application No. 15/839,073, filed on Dec. 12, 2017, now Pat. No. 10,069,027.

(60) Provisional application No. 62/559,336, filed on Sep. 15, 2017.

(51) Int. Cl.
    *G01N 21/00* (2006.01)
    *H01L 31/024* (2014.01)
    *H01L 31/107* (2006.01)
    *C12N 5/076* (2010.01)
    *G01J 1/44* (2006.01)
    *G01N 15/10* (2006.01)

(52) U.S. Cl.
    CPC ..... *G01N 15/1436* (2013.01); *G01N 15/1459* (2013.01); *G01N 21/00* (2013.01); *G01N 21/645* (2013.01); *H01L 31/024* (2013.01); *C12N 5/061* (2013.01); *C12N 2529/10* (2013.01); *G01J 2001/4453* (2013.01); *G01N 2015/1006* (2013.01)

(56) References Cited

U.S. PATENT DOCUMENTS

| | | | |
|---|---|---|---|
| 2003/0092058 A1* | 5/2003 | Spaulding | G01N 15/1404 435/7.1 |
| 2004/0053243 A1* | 3/2004 | Evans | G01N 21/17 435/6.19 |
| 2005/0112541 A1 | 5/2005 | Durack et al. | |
| 2011/0089340 A1 | 4/2011 | Merchez et al. | |
| 2012/0307244 A1 | 12/2012 | Sharpe et al. | |
| 2015/0024385 A1* | 1/2015 | Parrish | G01N 33/5091 435/6.1 |
| 2016/0076083 A1* | 3/2016 | Ellington | C12Q 2527/101 506/9 |
| 2016/0370278 A1 | 12/2016 | Muir | |

OTHER PUBLICATIONS

Luminex 200 System User Manual, Luminex Corporation, PN 89-00002-00-109, Rev. A., 60 pages Jul. 2005.

\* cited by examiner

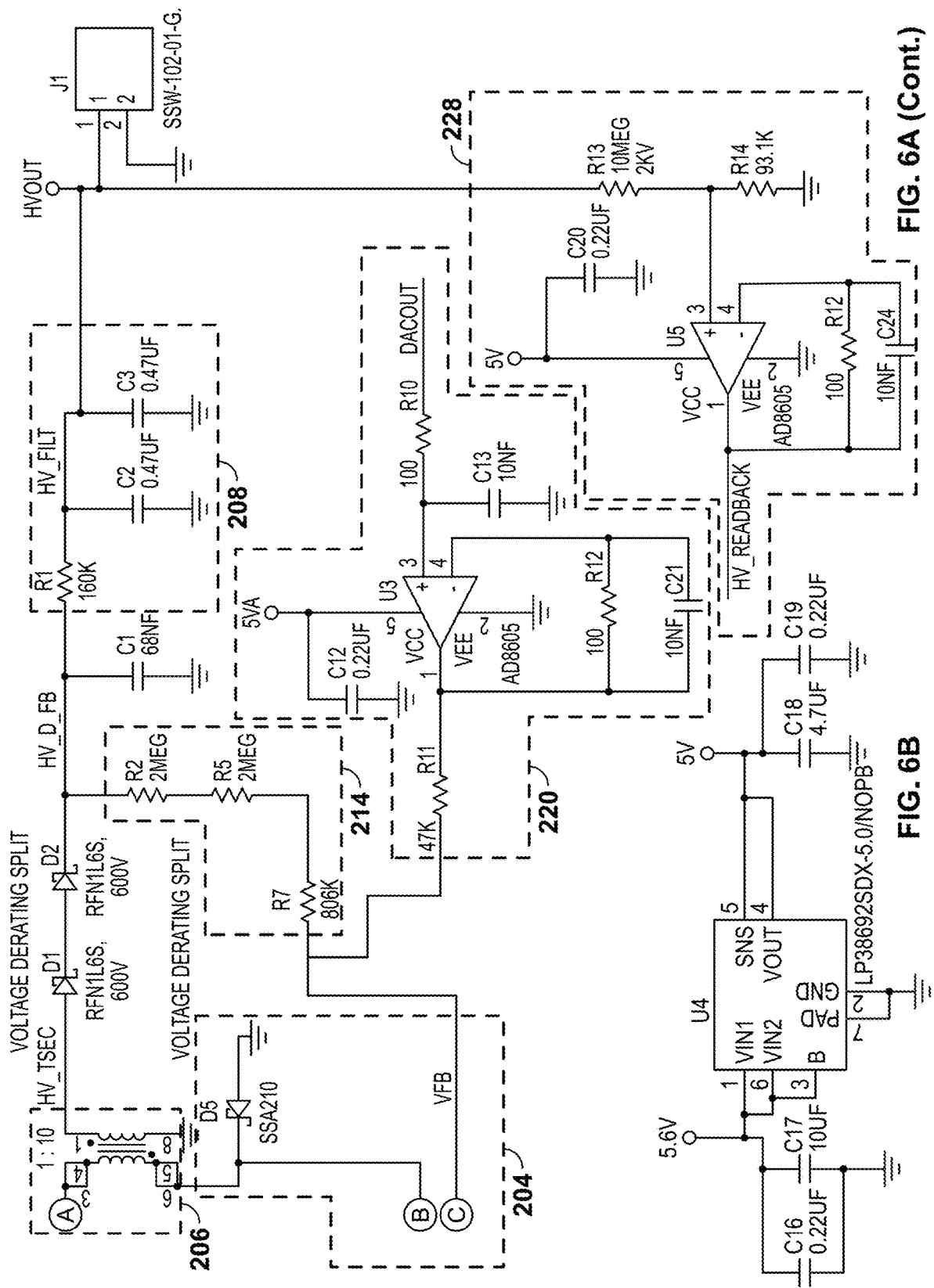

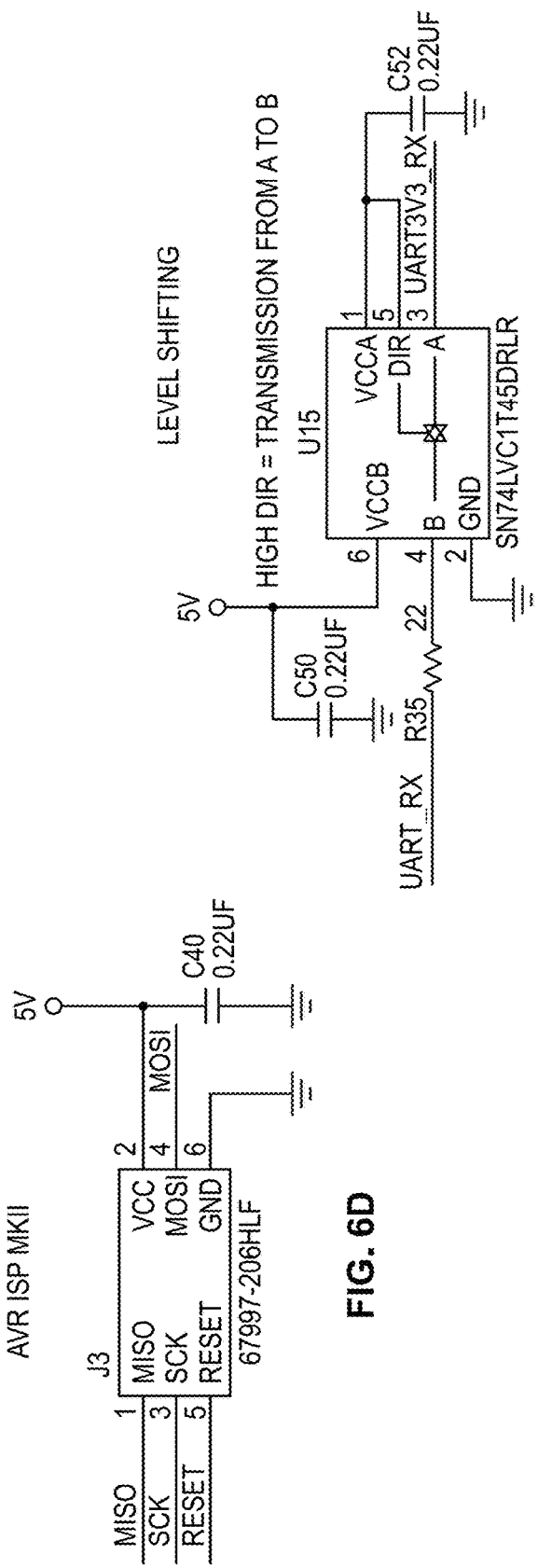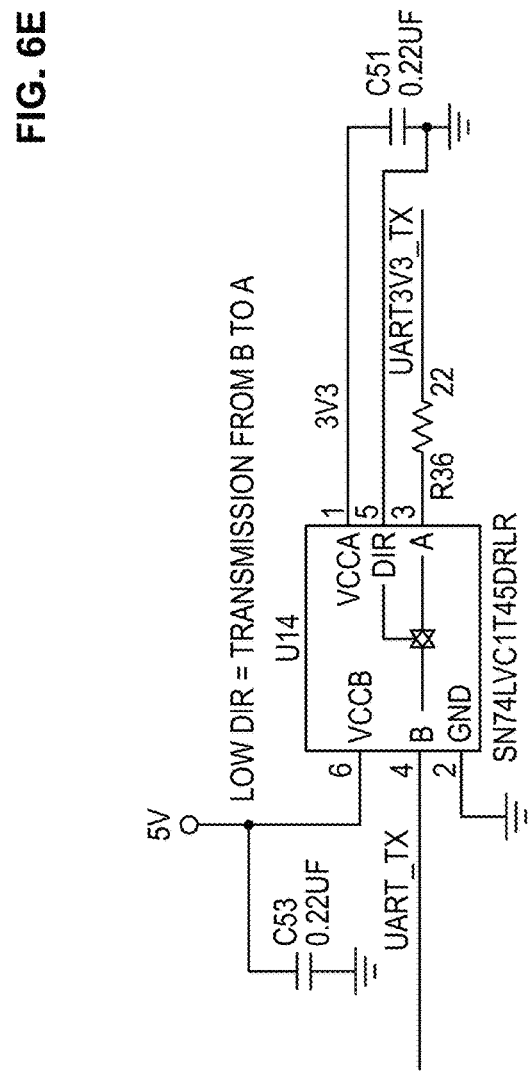

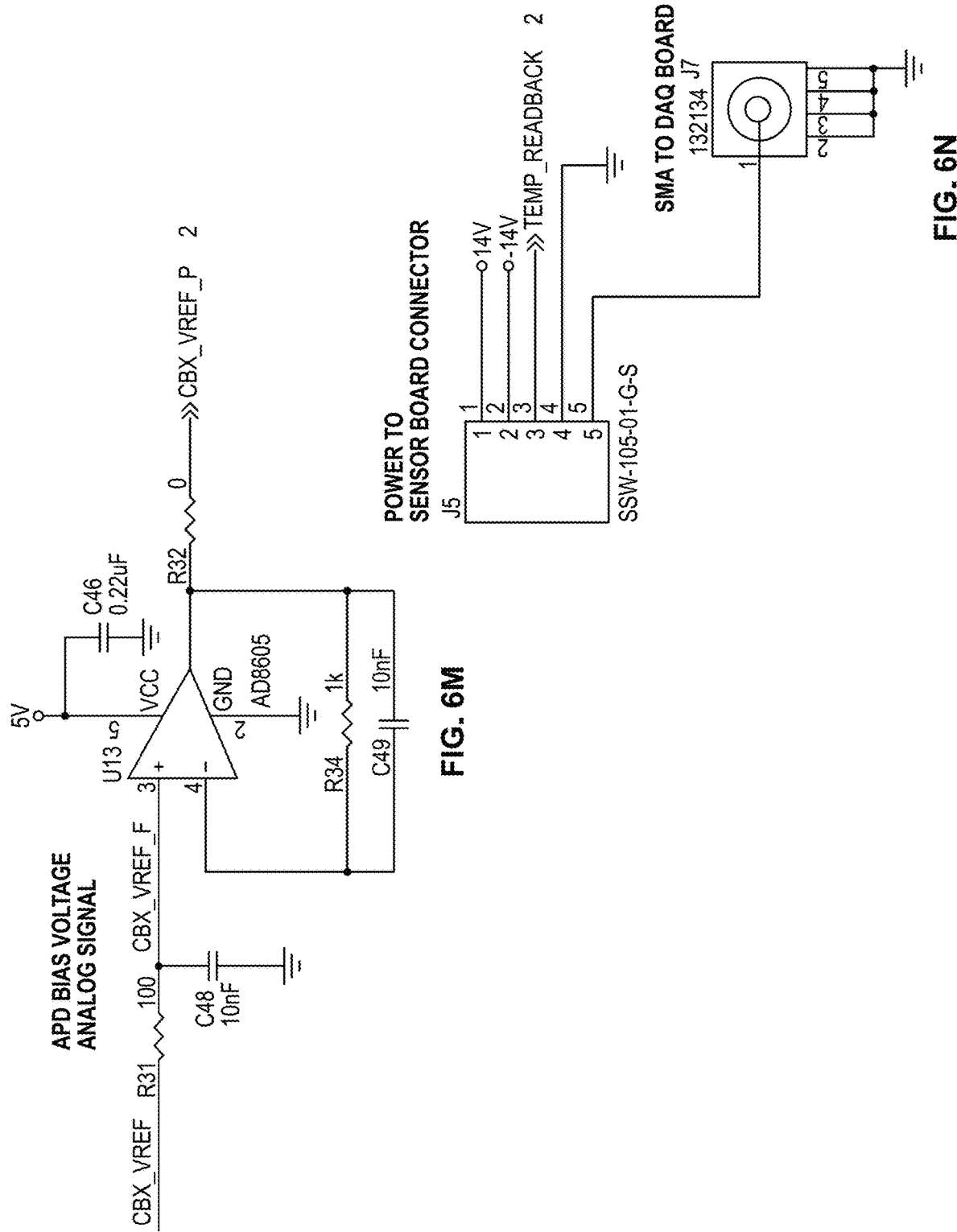

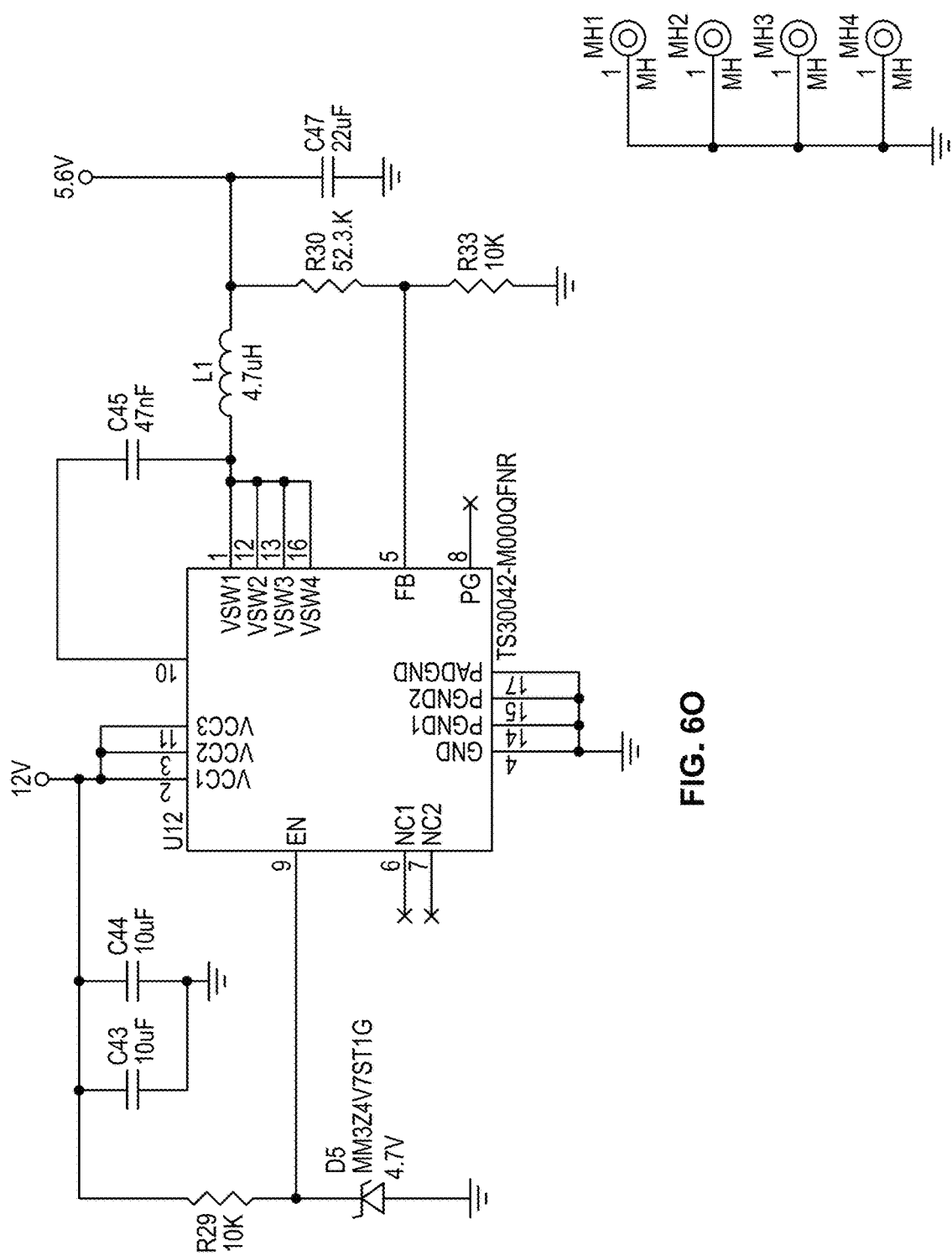

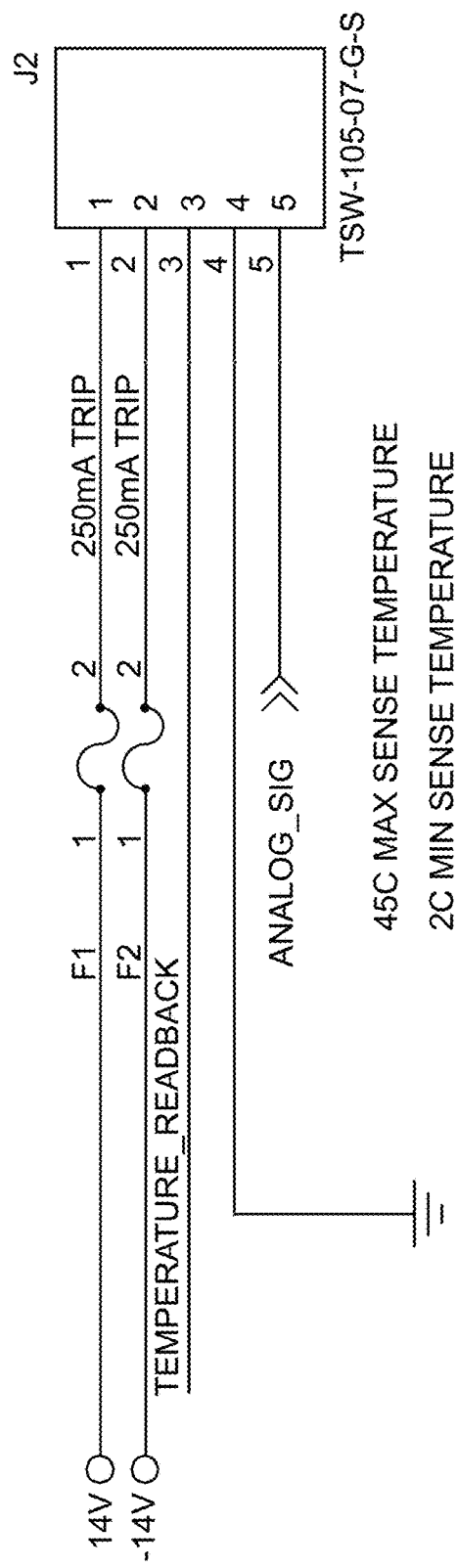
FIG. 6T
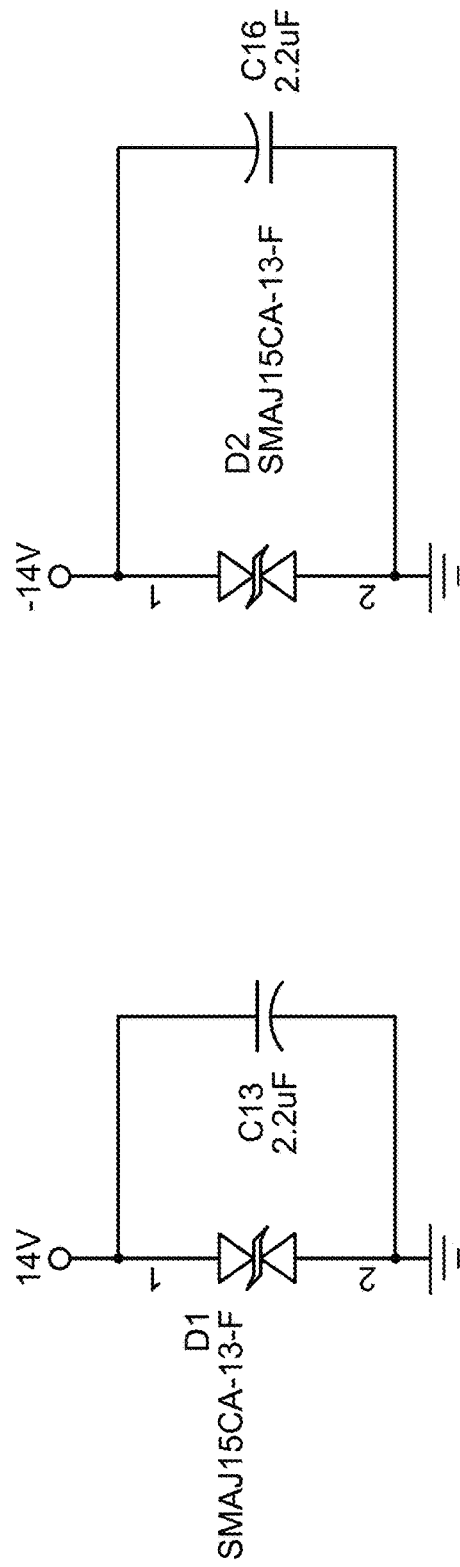
FIG. 6V
FIG. 6U ent may be processed (for example, digitized and analyzed by a processor) to assess the chromosomal content of the sperm cell.

One consideration when using a flow cytometer to perform this type of differentiation may be the sensitivity of the light-sensing componentry of the cytometer. The amount of light emitted (that is, the number of photons emitted) by a single cell that has been stained with a fluorescent, DNA-intercalating dye may be relatively low. As a result, the detection componentry must be sufficiently sensitive, both in order to make the detection, and even more so in order to detect differences in certain characteristics between different cells.

Cytometer technology may implement a PMT to achieve sufficient sensitivity for an application such as determining the chromosomal content of sperm cells. The PMT's relatively large optical signal gains (for example, $10^7$ or greater) enable this particular application. For example, PMTs with such optical gain may be capable of sensing a sufficiently low level of light emission, and of discriminating the roughly 3% difference in total fluorescence between stained XX-chromosome and XY-chromosome bearing sperm cells. However, PMTs are relatively expensive. They may also require a relatively long period of time to "warm up" (during which the PMT should not be exposed to light) once the flow cytometer has been turned on. Additionally, a PMT may require voltage in the thousands of volts. Furthermore, a PMT may require a shutter to block light when not in use, as normal room lighting can damage and break the PMT if exposed.

METHODS OF SPERM CELL SENSING UTILIZING AN AVALANCHE PHOTODIODE AND CYTOMETER APPARATUS

CROSS REFERENCE TO RELATED APPLICATIONS

This application is a divisional of U.S. patent application Ser. No. 16/403,170, filed on May 3, 2019, which is a continuation of Ser. No. 16/056,003, filed on Aug. 6, 2018, now U.S. Pat. No. 10,333,018, issued Jun. 25, 2019, which is a continuation of Ser. No. 15/839,073, filed on Dec. 12, 2017, now U.S. Pat. No. 10,069,027, issued Sep. 4, 2018, which claims the benefit of U.S. Provisional Patent Application No. 62/559,336, filed on Sep. 15, 2017, the entireties of which are herein incorporated by reference.

BACKGROUND

Generally, this application relates to flow cytometry. In particular, this application relates to techniques for implementing an avalanche photodiode in a cytometer to detect the sex of a sperm cell.

Flow cytometry may utilize light detection to assess characteristics of particles, such as cells, flowing through the cytometer. In certain applications, a cytometer may detect light emitted by cells, including light emitted by fluorescent, DNA-intercalating dye. The ability to detect such emitted light may permit accurate and sensitive differentiation of certain characteristics of the cells.

One such application is the determination of whether a sperm cell has two X-chromosomes (which may produce a female zygote) or alternatively an X-chromosome and a Y-chromosome (which may produce a male zygote). A sperm cell with two X-chromosomes may have approximately 3% more DNA than a sperm cell with an X-chromosome and a Y-chromosome. By identifying the chromosomal content of a sperm cell, it may be possible to create a relatively high-purity population of XX or XY sperm cells. Such a population may be generated, for example, by keeping the desired gender and killing the undesired one (or by segregating the two genders). The substantially high-purity population may be used to inseminate a female animal (such as bovids, equids, ovids, goats, swine, dogs, cats, camels, elephants, oxen, buffalo, or the like) to obtain a desired male or female offspring, with relatively high probability.

The characteristics of the chromosomes may be identified by staining the DNA of sperm cells with a fluorochrome (for example, a DNA-intercalating dye). The stained sperm cells may be forced to flow in a narrow stream or band and pass by an excitation or irradiation source such as a laser beam. As the stained sperm cells (a plurality of particles) are irradiated, the fluorochrome in the plurality of particles emits a responsive fluorescent light. The amount of fluorescent light may vary based at least in part on a relative amount of at least one particle differentiation characteristic (for example, the relative amount of chromosomes) present in each of the plurality of particles. The fluorescent light may be received by one or more optical elements that ultimately focus the received light onto a detection component, such as a photomultiplier tube ("PMT"). The detection component may generate an electrical, analog signal in response to the received light. The analog signal may vary in correspondence with the amount of received light. This signal may

SUMMARY

According to certain inventive techniques, a cytometer includes an avalanche photodiode, a switching power supply, a filter, and voltage adjustment circuitry. The switching power supply includes a feedback loop. The filter is electrically connected between the switching power supply and the avalanche photodiode. The voltage adjustment circuitry adjusts a voltage on the feedback loop based at least in part on a voltage measured between the filter and the avalanche photodiode.

The cytometer may further include a temperature sensor configured to sense a temperature and generate a corresponding temperature signal encoding temperature data, wherein the voltage adjustment circuitry is further configured to adjust the voltage on the feedback loop based at least in part on the temperature data and the voltage measured between the filter and the avalanche photodiode. The voltage adjustment circuitry may further be configured to adjust the voltage on the feedback loop based at least in part on at least one characteristic of the avalanche photodiode, the temperature data, and the voltage measured between the filter and the avalanche photodiode. The voltage adjustment circuitry may further be configured to adjust the voltage on the feedback loop based at least in part on at least one characteristic of the avalanche photodiode and the voltage measured between the filter and the avalanche photodiode. The voltage adjustment circuitry may include: an analog-to-digital converter configured to convert the voltage measured between the filter and the avalanche photodiode into a digital measured signal encoding measured voltage data; a processor configured to process at least the measured voltage data to generate a digital adjustment signal; and a digital-to-analog converter configured to convert the digital adjustment signal to an adjustment voltage, wherein the adjustment voltage influences the voltage on the feedback loop.

The processor may be configured to process at least temperature data and the measured voltage data to generate the digital adjustment signal. The processor may be configured to process at least temperature data, data corresponding to at least one characteristic of the avalanche photodiode, and the measured voltage data to generate the digital adjustment signal. The at least one characteristic of the avalanche photodiode may include at least one of a breakdown voltage and a reverse bias voltage corresponding to a predetermined optical gain. The cytometer may further include: a first amplifier configured to amplify a voltage at an anode of the avalanche photodiode to form a first amplified voltage; and a second amplifier configured to amplify the first amplified voltage to generate a second amplified voltage. The power supply may include a DC/DC power supply. The avalanche photodiode may be: arranged to receive an amount of fluorescent light emitted by each of a plurality of particles; the amount of received fluorescent light may vary based at least in part upon a relative amount of at least one particle differentiation characteristic present in each of the plurality of particles; and the avalanche photodiode may be configured to convert the amount of received fluorescent light into at least one signal which varies based upon the amount of received fluorescent light.

According to certain inventive techniques, a method includes: receiving an input voltage at input circuitry of a power supply; transforming, with a transformer, a voltage supplied by the input circuitry into a transformed voltage; receiving, at output circuitry of the power supply, the transformed voltage; generating, by the output circuitry, an output voltage; feeding back a feedback voltage corresponding to the output voltage to the input circuitry; receiving the output voltage at a filter; generating, by the filter, a filtered voltage; receiving the filtered voltage at an avalanche photodiode; receiving the filtered voltage at voltage adjustment circuitry; and adjusting the feedback voltage by the voltage adjustment circuitry according to at least the filtered voltage. The method may further include generating, by a temperature sensor, a temperature signal corresponding to a measured temperature, wherein said adjusting the feedback voltage further comprises adjusting the feedback voltage by the voltage adjustment circuitry according to at least the filtered voltage and the measured temperature. Said adjusting the feedback voltage further may include adjusting the feedback voltage by the voltage adjustment circuitry according to at least the filtered voltage, the measured temperature, and at least one value corresponding to a characteristic of the avalanche photodiode. Said adjusting the feedback voltage further may include adjusting the feedback voltage by the voltage adjustment circuitry according to at least the filtered voltage and at least one value corresponding to a characteristic of the avalanche photodiode. Said adjusting the feedback voltage may further include: converting, with an analog-to-digital converter, the filtered voltage into a digital measured signal encoding filtered voltage data; processing, with a processor, at least the filtered voltage data to generate a digital adjustment signal; converting, by a digital-to-analog converter, the digital adjustment signal to an adjustment voltage; and adjusting the feedback voltage according to the adjustment voltage. Said processing at least the filtered voltage data may further include processing at least temperature data and the filtered voltage data to generate the digital adjustment signal. Said processing at least the filtered voltage data may further include processing at least data corresponding to at least one characteristic of the avalanche photodiode, temperature data, and the filtered voltage data to generate the digital adjustment signal. The at least one characteristic of the avalanche photodiode may include at least one of a breakdown voltage and a reverse bias voltage corresponding to a predetermined optical gain. The method may further include: amplifying, with a first amplifier, a voltage at an anode of the avalanche photodiode to form a first amplified voltage; and amplifying, with a second amplifier, the first amplified voltage to generate a second amplified voltage. The input circuitry, the transformer, and the output circuitry may comprise a DC/DC power supply.

According to certain inventive techniques, a flow cytometry apparatus includes: a flow chamber configured to direct a fluid stream including sample particles through a particle interrogation location; a laser configured to emit electromagnetic radiation along a beam path to the particle interrogation location; an avalanche photodiode configured to: receive electromagnetic radiation from the interrogation location; and output a time-varying analog signal indicative of an intensity of the received electromagnetic radiation; at least one amplifier configured to amplify the time-varying analog signal; an analog-to-digital converter configured to receive the amplified time-varying analog signal and produce a corresponding digitized output signal; and a processor configured to analyze the digitized output signal.

According to certain inventive techniques, a method for analyzing sperm cells contained in a fluid stream as the sperm cells flow through an interrogation location includes: emitting electromagnetic radiation from a laser; illuminating, with the electromagnetic radiation emitted by the laser, the fluid stream and the sperm cells contained therein; detecting, with an avalanche photodiode, electromagnetic radiation emitted from the interrogation location; generating, by the avalanche photodiode, a time-varying analog signal indicative of an intensity of the detected electromagnetic radiation; converting, with an analog-to-digital converter, the time-varying analog signal into a corresponding digital signal; and analyzing, by a processor, the digital signal to determine characteristics of the sperm cells in the fluid stream.

According to certain inventive techniques, a method for assessing an amount of DNA within a nucleus of a sperm cell includes: staining the DNA within the nucleus of the sperm cell; irradiating the stained DNA within the nucleus of the sperm cell; and detecting, with an avalanche photodiode, fluorescent light emitted from the irradiated and stained DNA within the nucleus of the sperm cell. The method may further include differentiating X chromosome bearing sperm cells and Y chromosome bearing sperm cells by: determining a sex of a sperm cell using the detected amount of DNA within the nucleus of the sperm cell; and differentiating between a plurality of sperm cells based upon said sex determination. The characteristics of the sperm cells may include corresponding amounts of DNA within the nuclei of the sperm cells. The method may further include deactivating a given sperm cell based upon the determined amount of DNA within the nucleus of the given sperm cell. Said deactivating may include photo-damaging the given sperm cell. The method may further include: forming droplets a plurality having one of said sperm cells entrained; charging each of said droplets differentially based upon said sex differentiation characteristic of said sperm cells entrained in said droplets; deflecting each of said droplets; and differentially collecting each of said droplets based upon said sex differentiation characteristic of said sperm cells entrained in said droplets.

Figure 1:
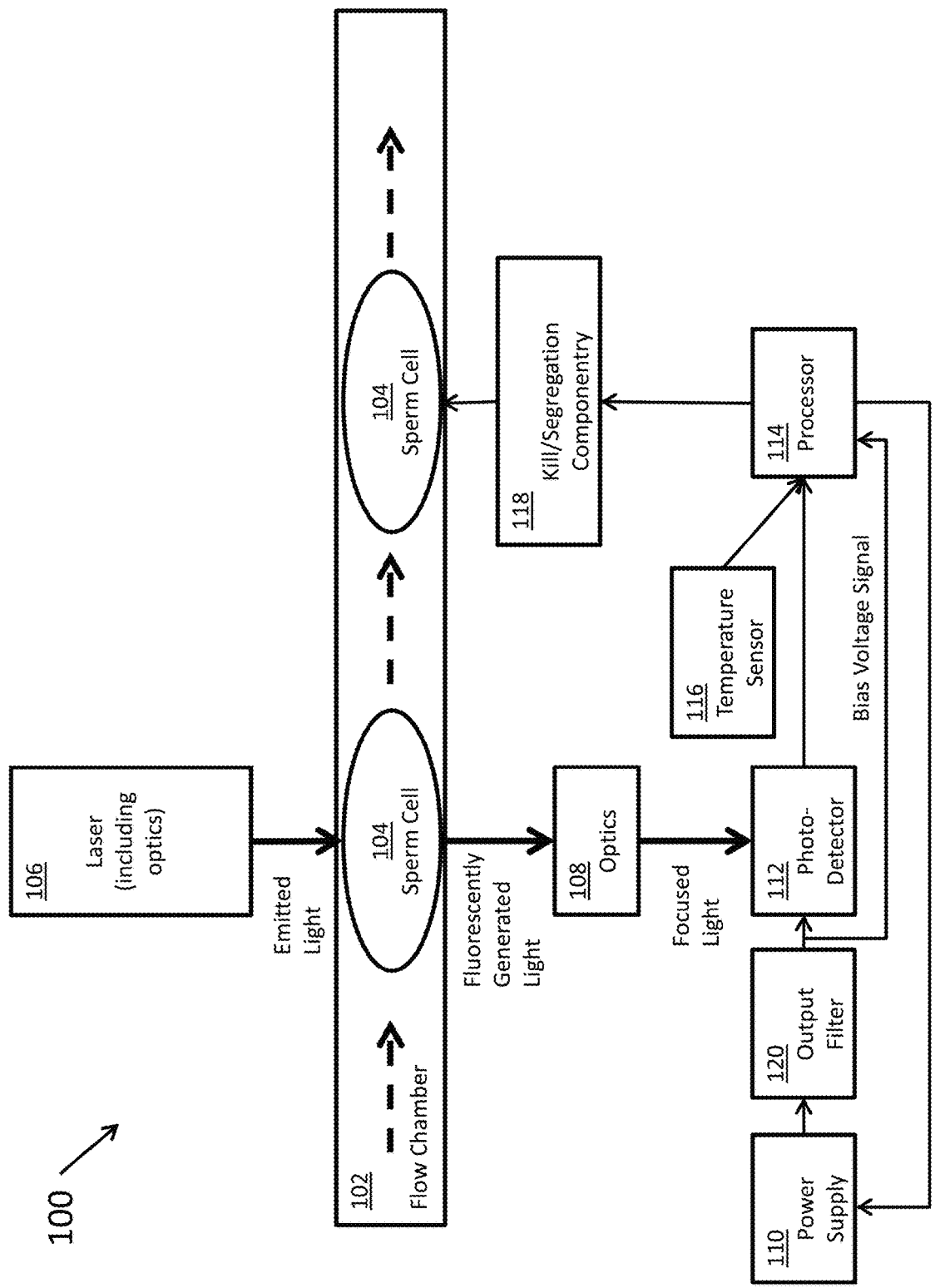
FIG. 1 illustrates a flow cytometer, according to certain inventive techniques.

The foregoing summary, as well as the following detailed description of certain techniques of the present application, will be better understood when read in conjunction with the appended drawings. For the purposes of illustration, certain techniques are shown in the drawings. It should be understood, however, that the claims are not limited to the arrangements and instrumentality shown in the attached drawings.

DETAILED DESCRIPTION

Certain inventive techniques discussed herein describe a cytometer that uses an avalanche photodiode ("APD") with a lower cost implementation instead of a PMT to obtain low-level fluorescence detection, such that bull sperm chromosomal content can be determined or differentiated. The advantageous techniques may also enable the use of an APD in other cytometer sensing applications. An APD has substantial advantages over a PMT, including, for example, lower cost, no "warm-up" period, smaller and more efficient active area, improved control over the detection component, lower bias voltage (hundreds of volts vs. thousands of volts for a PMT), and no need for a light-blocking shutter when not in use.

With regard to the active area, a PMT may have a relatively large active area (in one example, approximately 13.7 mm×3.9 mm) whereas an exemplary APD may have a substantially smaller and more symmetrical active area (in one example, a circular area having a 1 mm diameter). This may result in an improved fill factor for the sensor (for example, one order of magnitude or greater). By improving fill factor, it is easier to align the APD (versus the PMT) with the laser beam cross-sectional area, which makes the optical alignment relatively easier when constructing a system.

With regard to improved control over the APD (versus the PMT), certain inventive techniques described herein allow for improved compensation and biasing, for example, by incorporating the APD into the cytometer in a manner that leverages the APDs quantum efficiency combined with the sensor optical gain. The quantum efficiency of the APD is related to the cytometer through a chosen dye and optical excitation wavelength. The optical gain factor of the APD may combine with the quantum efficiency, which is cell-stain (dye) dependent to produce the sensor output signal.

According to certain inventive techniques, the APD is configured as an element of the voltage supply output filter network. Furthermore, the cytometer may include temperature compensation circuitry. APD optical gain may vary with temperature. If the temperature change is known, the bias voltage on the APD may be adjusted to compensate for the temperature change (to keep gain substantially constant). Alternatively, a heater that keeps the APD at constant temperature, or a relatively giant thermal mass, or a thermal electric cooler could also be used to stabilize the APD temperature (and thus keep the APD optical gain substantially constant).

According to certain inventive techniques, APD conditioning circuitry may employ a two-stage feedback network to achieve relatively low noise performance. The first stage may be an analog stage controlled by a resistive feedback circuit to a flyback converter in a high-voltage power supply that reverse-biases the APD. The resistive feedback circuit in the power supply may have a digital-to-analog converter connected through circuitry that provides the ability to change the output voltage of the flyback converter. The second stage may allow the APD to become a part of an output filter network of the high-voltage power supply. The second stage may be designed to take into consideration that the flyback converter feedback may not accurately represent the voltage at the APD due to relatively large output filtering used to achieve low noise performance. The second stage feedback network may measure the output voltage after the first output filter stage and digitize it, becoming a digital feedback element in the control loop. This configuration may combine both analog and digital feedback elements in a hybridized implementation. By using the second stage feedback network, relatively large values in the output filtering, such as relatively large pole compensation generating relatively large resistor and capacitor combinations, may be able to be used for improved noise filtering through the use of both the analog and digital feedback mechanisms.

The second stage feedback network may operate by sensing the voltage after a first output filter stage of the high-voltage power supply. This may take into consideration the voltage substantially near or at the APD. The sensed voltage may be digitized and processed by a processor (for example, a single processor or a plurality of processors or processing elements working together) in a substantially real-time manner. The processor may evaluate the sensed voltage proximate the APD (after the first output filter) as well as, optionally, other parameters such as the APD temperature and characteristics particular to a given APD (for example, APD reverse voltage VR or breakdown voltage VBR). The processor then may output a value that is converted into an analog signal. This signal may be used to influence the voltage at the feedback node of the flyback converter.

As will be further described, the second stage feedback may be generated using an attenuated output voltage read back through an analog-to-digital converter (for example, 16-bit). This same analog-to-digital converter (or a separate analog-to-digital converter) may also be used to read in temperature data from the APD operating environment.

FIG. 1 shows a flow cytometer 100, according to certain inventive techniques. A stream of sperm cells 104 may pass through a flow chamber 102, such that they may be single-file in certain strategic locations. The flow chamber may direct a fluid stream including the sperm cells 104 (sample particles) through a particle interrogation location. The sperm cells 104 may have been previously stained with a dye, such as a DNA-intercalating dye. Such a dye may fluoresce (or cause fluorescence) as it generates responsive light in response to being exposed to a light (or electromagnetic radiation) source. As the dyed sperm cells 104 pass one-by-one, they may be exposed to a beam of electromagnetic radiation (for example, light of a given wavelength) generated by a laser and emitted along a beam path (and optionally associated optics 106) to the particle interrogation location. Such associated optics may include lenses, filters, or the like. The exposure of the dye to the laser light may cause the dye to emit fluorescently generated light. The amount of fluorescently generated light may vary by a detectable degree, depending on whether the sperm cell 104 carries XX chromosomes or XY chromosomes.

The fluorescently generated light may be received by optics 108 (for example, lenses, filters, or the like), and it may be focused onto an active area of a photodetector 112. According to certain inventive techniques, the photodetector 112 may include an APD. The photodetector 112 may generate an output signal that corresponds (varies linearly or non-linearly) to the amount of electromagnetic radiation (for example, light of a given wavelength) that it receives from the interrogation location. The photodetector output signal may include a time-varying analog signal indicative of an intensity of the received electromagnetic radiation. This photodetector output signal may ultimately be communicated to a processor 114 (which may include one processor or a plurality of processors that control a portion of the operation or the entire operation of the flow cytometer 100). The photodetector output signal may be amplified by at least one amplifier (or two or more amplifiers in series) before it is communicated to the processor 114. Furthermore, the photodetector output signal (for example, as amplified) may be digitized before being communicated to the processor 114. A temperature sensor 116 may generate an output signal that corresponds (varies linearly or non-linearly) to the sensed temperature. As such, the temperature signal may encode temperature data that corresponds to a given sensed temperature. This temperature signal may ultimately be communicated to the processor 114 (for example, after amplification). The processor 114 may also receive a signal corresponding to the bias voltage (for example, the reverse-bias voltage) of the photodetector 112 generated by the power supply 110 and filtered by the output filter 120.

It should be understood that the photodetector signal, the temperature signal, and the bias voltage signal may be conditioned and/or digitized before they are received by the processor 114—that is, they need not be directly connected such that the exact voltages output by the sensors 112, 116 or the output filter 120 are delivered to the processor 114. Instead, the system need only be designed such that the information generated by the sensors 112, 116 and the bias voltage is communicated to the processor 114. In this sense, these signals are communicated to the processor 114.

Depending on the temperature signal, the bias voltage signal, and/or known photodetector 112 characteristics, the processor 114 may influence the voltage of the power supply 110 that conditions (for example, reverse-biases) the photodetector 112. Such known photodetector 112 characteristics may include an APD reverse voltage VR or breakdown voltage VBR. These characteristics may be stored in memory (not shown) which may be accessed by the processor 114 for computations. Such a memory may include a single memory or a plurality of memories separately addressable. The memory may be within a package with the processor or may be in a package external to the processor package. The memory may be non-volatile (for example, EEPROM or flash memory). The memory may also store relevant curves (for example, curves defining the input-output relationships of the photodetector 112 or the temperature sensor 116, or other characteristics within the flow cytometer 100).

The processor 114 may make a decision as to whether the sperm cell 104 carries XX or XY chromosomes (that is, female or male gendered sperm cells 104, respectively). If a sperm cell 104 does not carry the desired set of chromosomes, the processor 114 may control the kill/segregation componentry 118 to kill or segregate the unwanted sperm cell 104. In this manner, a substantially high-purity population of gender-specific sperm cells 104 may be generated.

Figure 2:
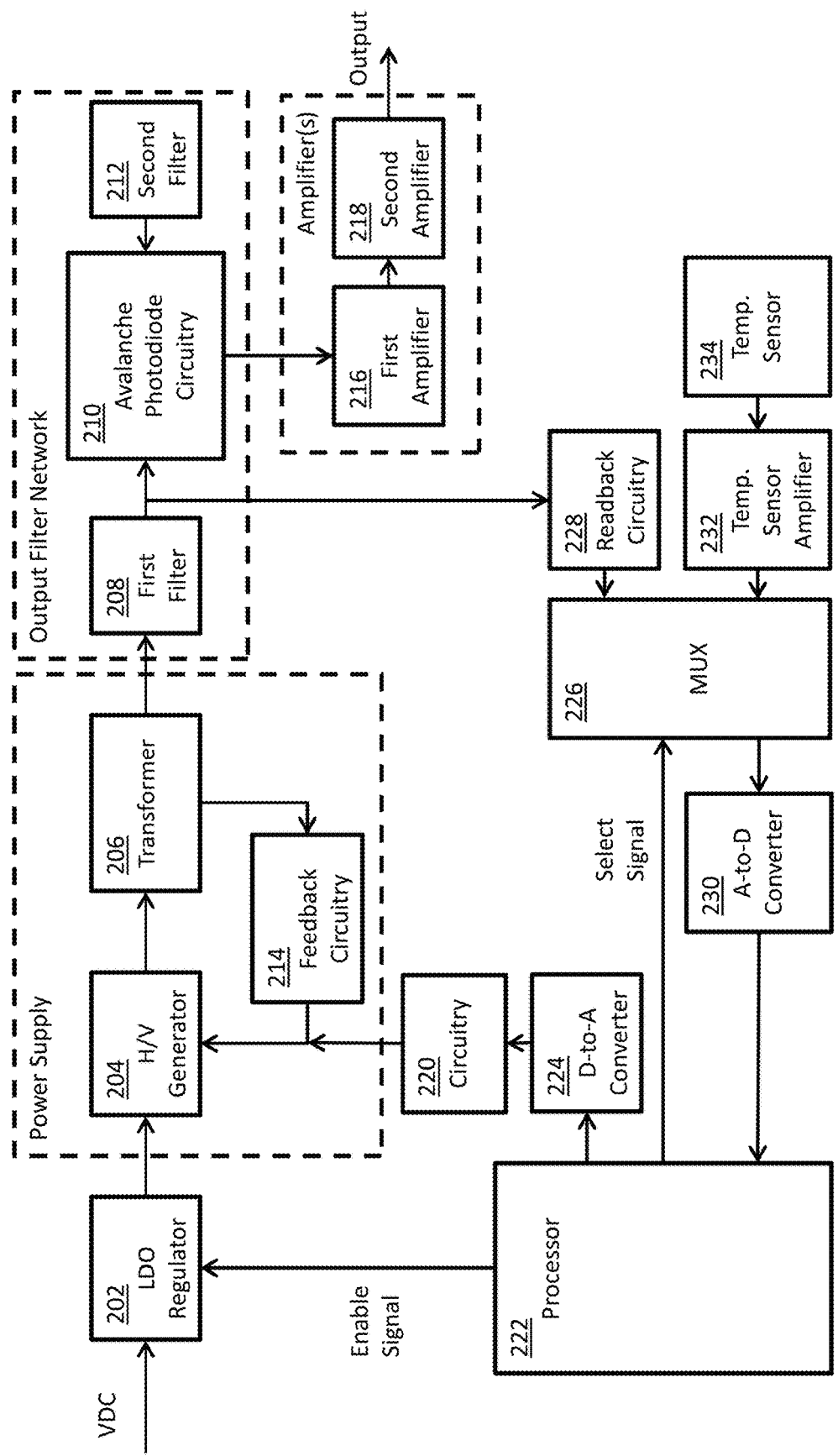
FIG. 2 shows a block diagram for circuitry capable of capable of detecting the chromosomal content of sperm cells using an avalanche photodiode, according to certain inventive techniques.
Figure 6A:
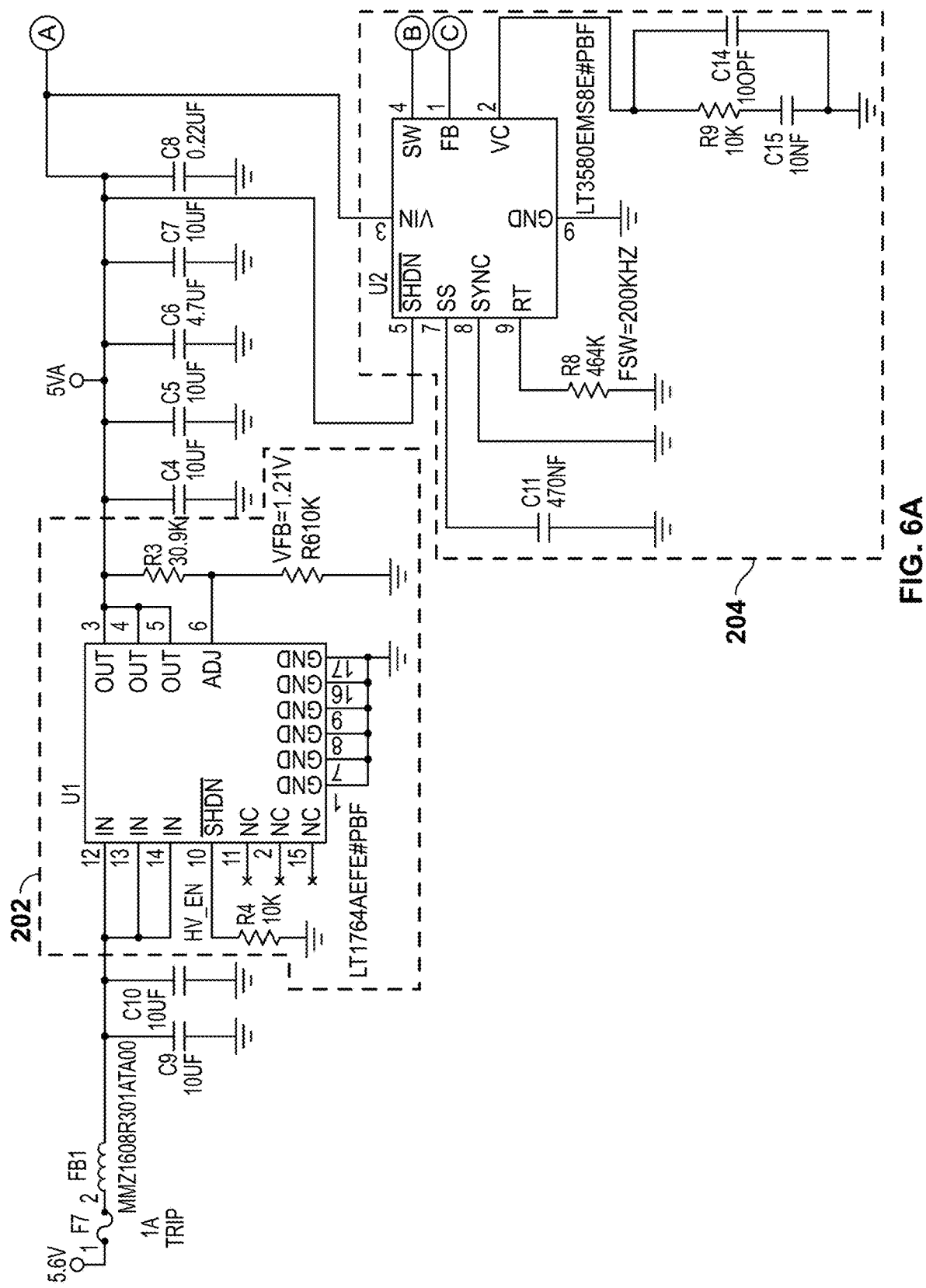
FIGS. 6A-6X depict circuit schematics for a portion of a cytometer, according to certain inventive techniques.
Figure 6C:
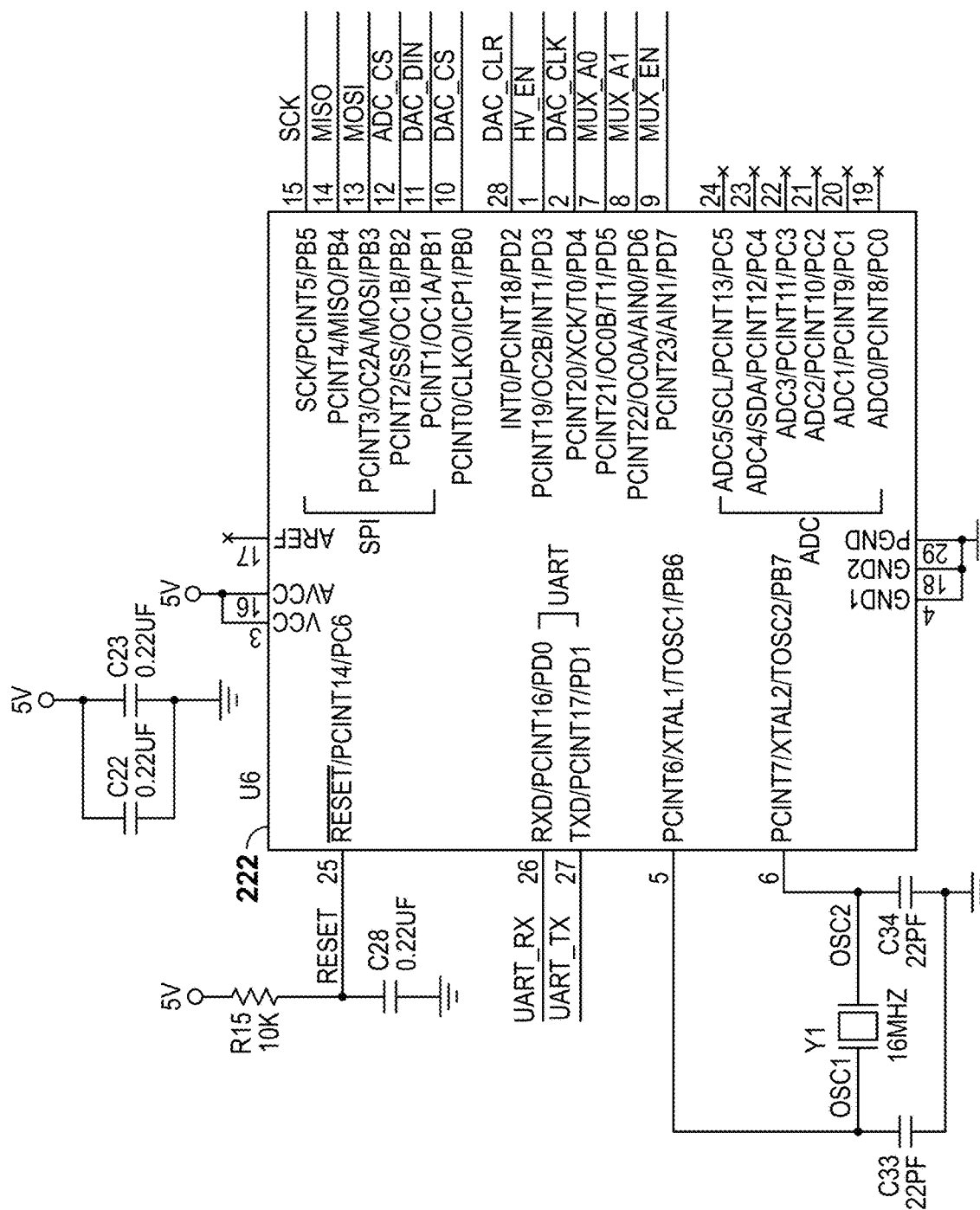
Figure 6G:
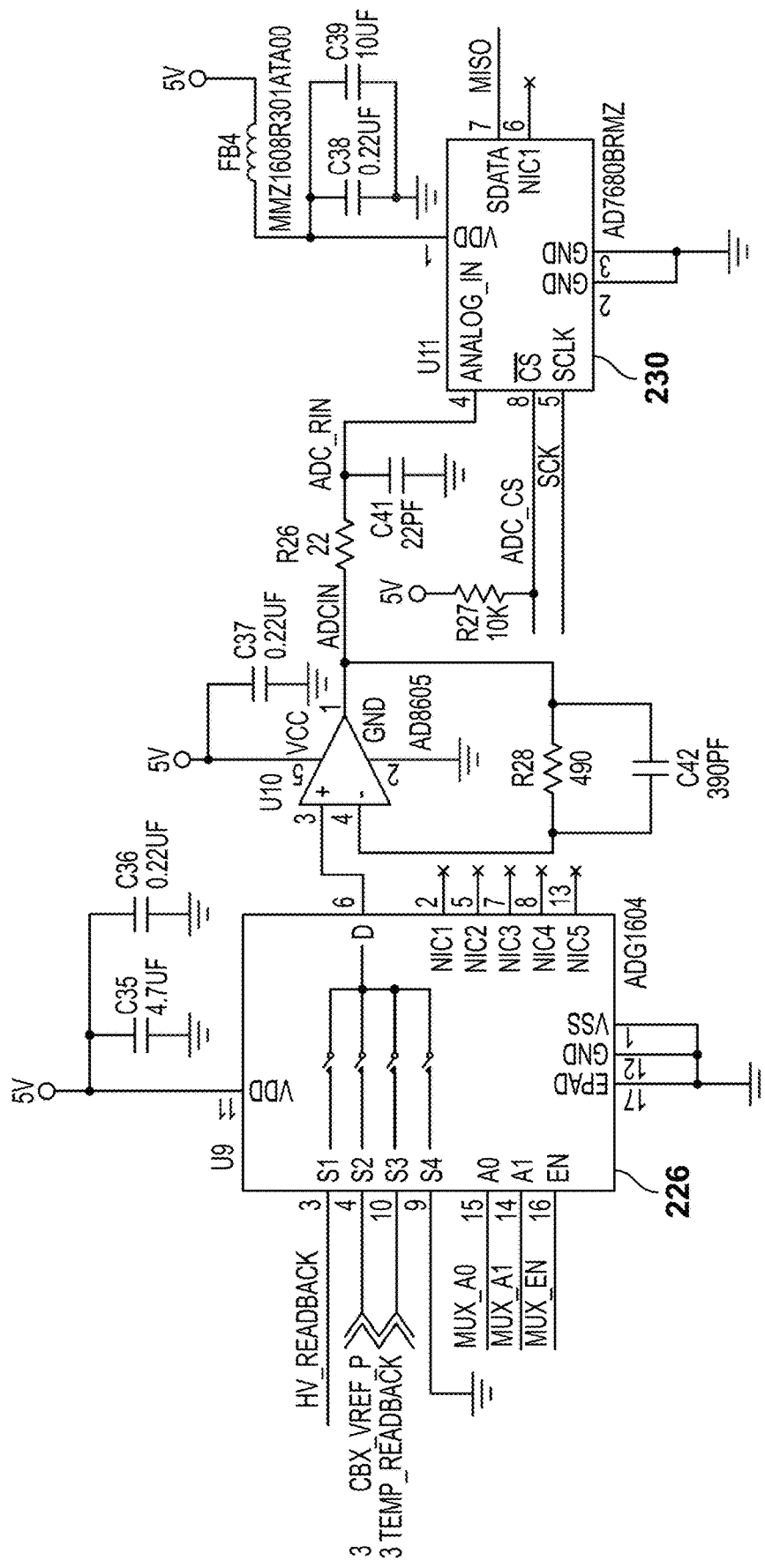
Figure 6H:
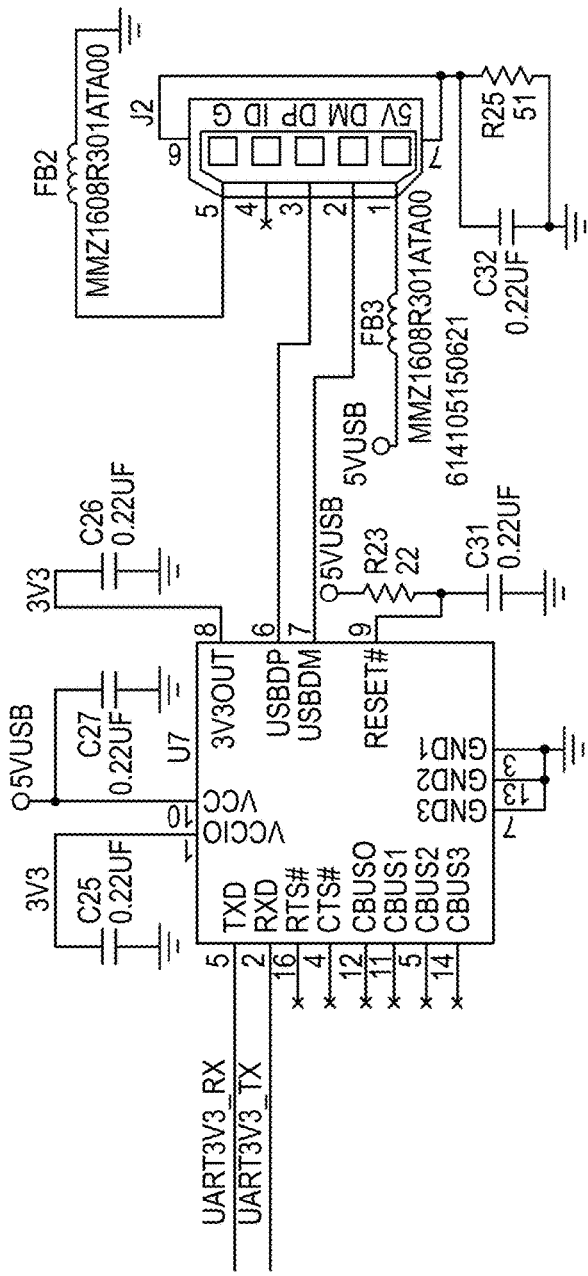
Figure 6I:
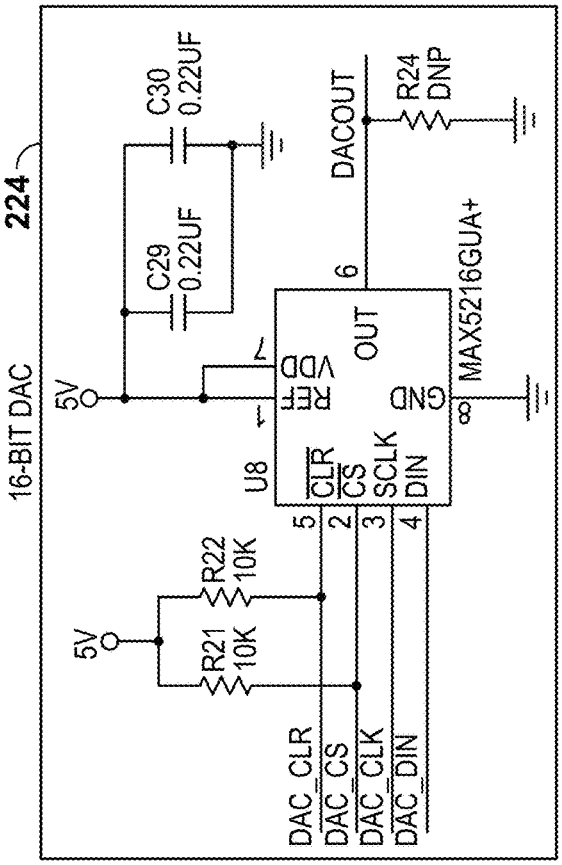
Figure 6J:
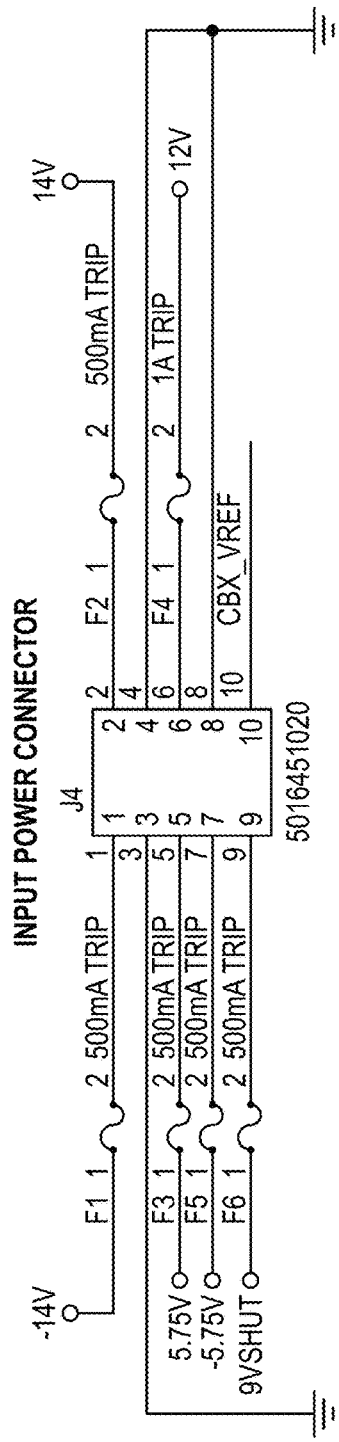
Figure 6K:
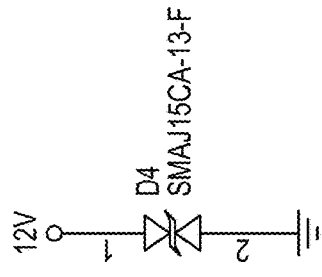
Figure 6L:
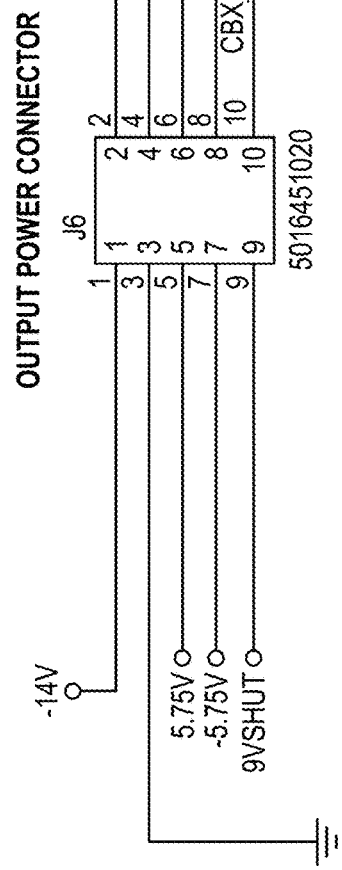
Figure 6Q:
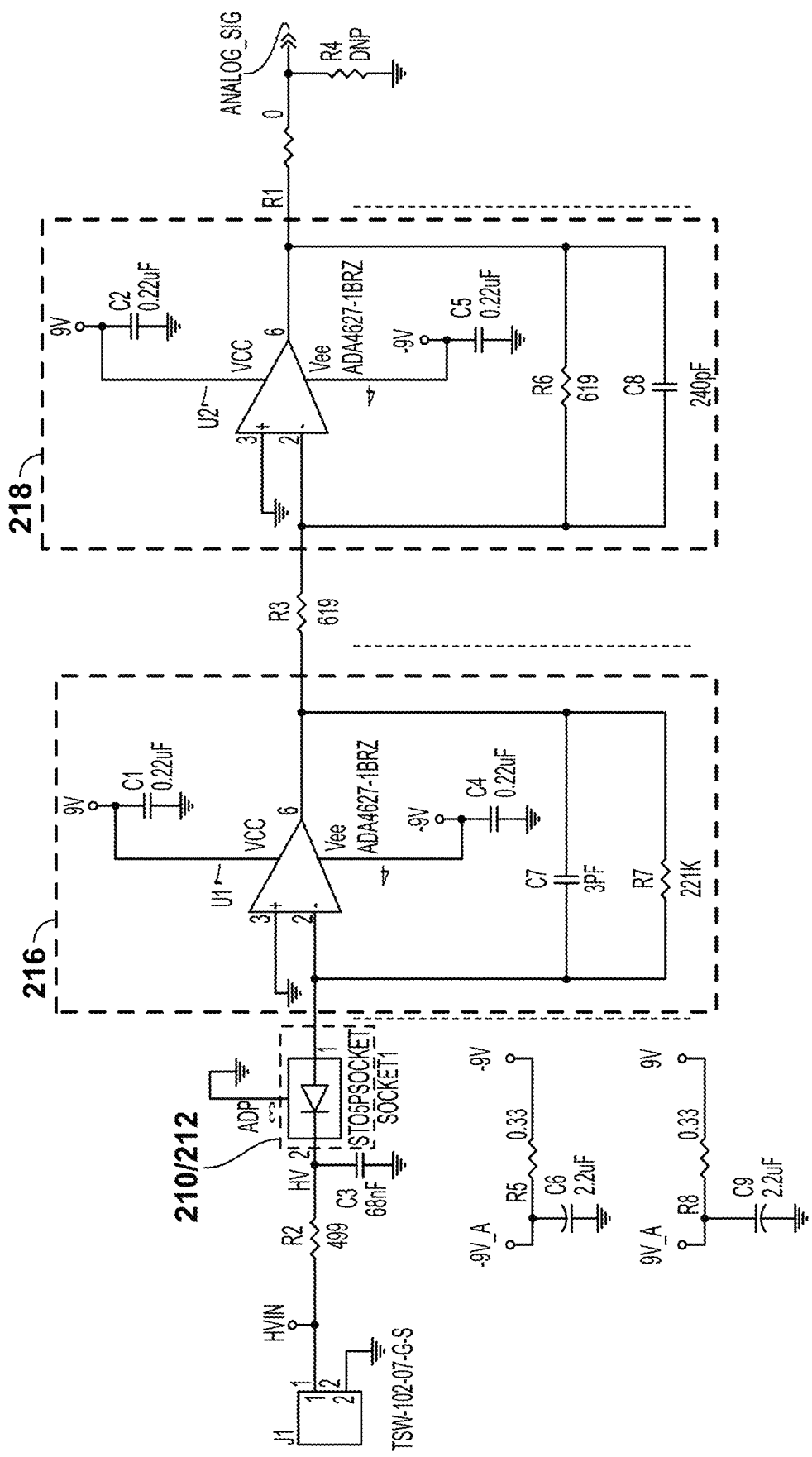
Figure 6R:
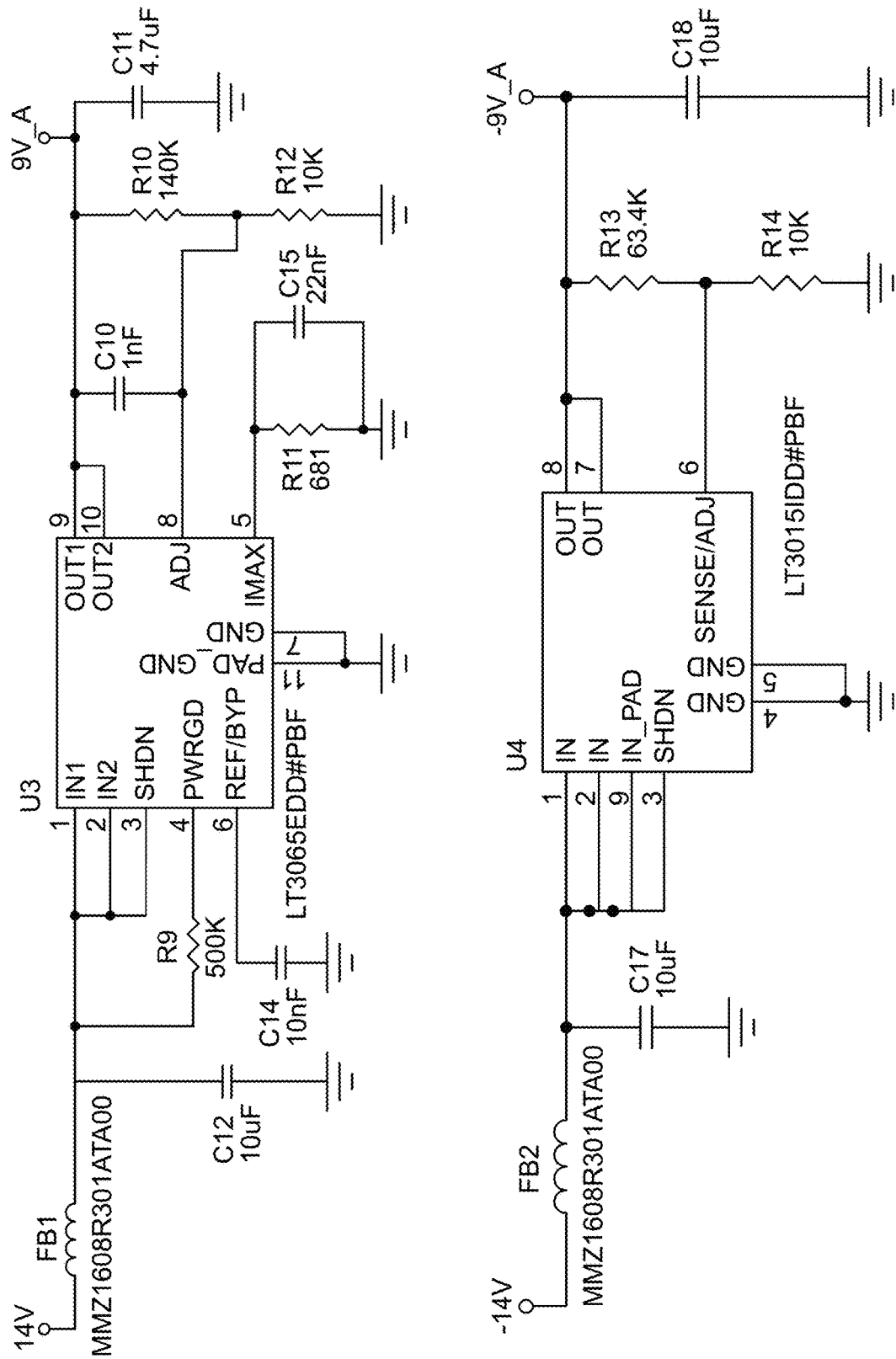
Figure 6S:
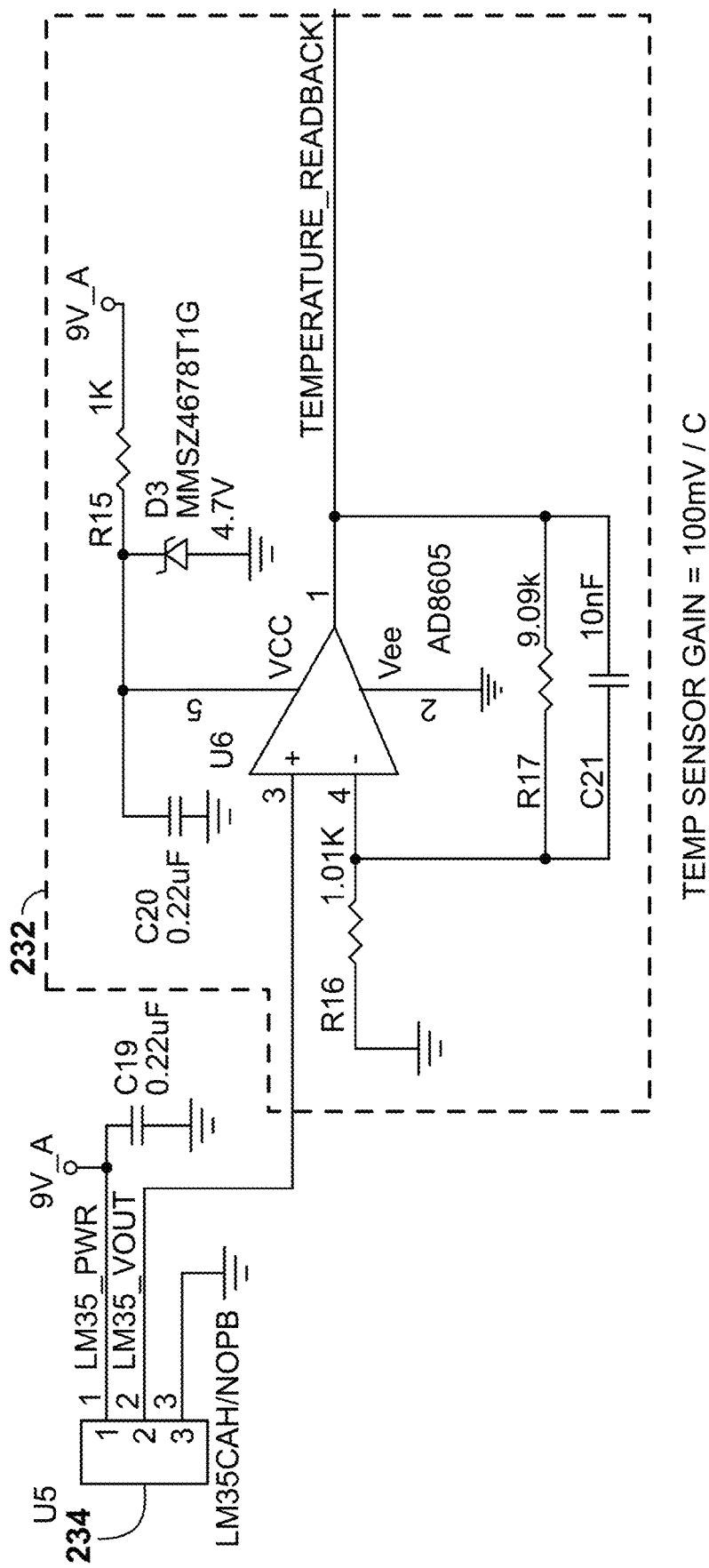
Figure 6X:
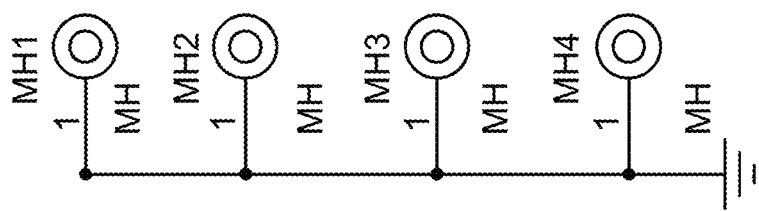
Figure 6W:
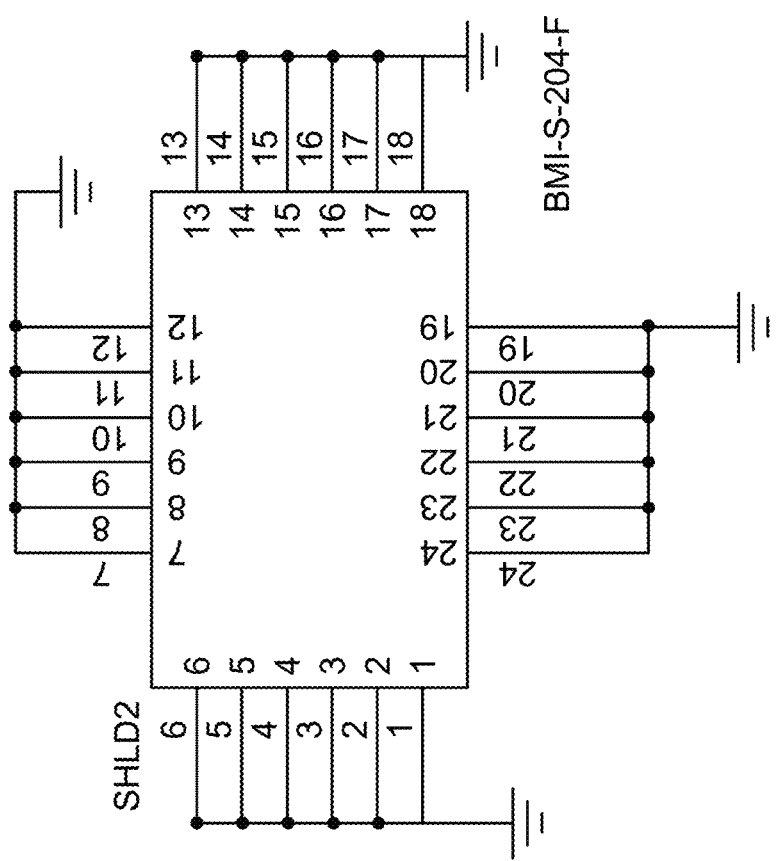

FIG. 2 shows a block diagram 200 for circuitry capable of detecting the chromosomal content of sperm cells using an avalanche photodiode ("APD"), according to certain inventive techniques. The block diagram 200 may generally correspond to elements 110, 112, 114, 116, and 120 depicted in FIG. 1 and discussed above. Furthermore, FIGS. 6A-6X depict circuit schematics (just one exemplary embodiment of many possibilities) that correspond to block diagram 200, according to certain inventive techniques.

Linear drop-out ("LDO") regulator circuitry 202 (for example, including an integrated circuit, such as Linear Technology's LT1764) may receive an input DC voltage and convert it to a regulated low voltage (e.g., substantially 5 VDC). This block provides pre-regulation for the high voltage that will be created downstream. This initial stage of regulation may improve system noise by removing a substantial amount of the switching residue from the upstream voltage supply.

The regulated low voltage output from the LDO circuitry 202 is received by high-voltage generator circuitry 204, which generates a relatively high voltage. Such circuitry 204 may include an integrated circuit (such as Linear Technology's LT3580). The output of the high-voltage generator circuitry 204 may be provided to the transformer 206. The transformer 206 may step the voltage up, for example, by a factor of 10. Schottky diode(s) (one or more in series) may receive the output of the transformer 206. The resulting voltage may be fed back to the high-voltage generator circuitry 204 through feedback circuitry 214 (for example, one or more resistors in series).

The high-voltage generator circuitry 204, the transformer 206, and the feedback circuitry 214 may form a power supply, such as a DC/DC boost switching power supply. The power supply may be a boost configuration that implements a resistive feedback circuit and the digital-to-analog converter 220 to generate the output voltage (as will be further explained).

Overall, the power supply may include input circuitry (for example, including the high-voltage generator circuitry 204), the transformer 206, and output circuitry (for example, including one or more Schottky diodes in series between the output of the transformer 206 and the first filter 208, or other suitable components). A feedback loop may communicate what the voltage is after the output circuitry to a feedback node arranged as an input to the high-voltage generator circuitry 204.

A first filter 208 may be located at the output of the power supply. The first filter 208 may include a network of one or more capacitor(s) and/or resistor(s). For example, the first filter 208 may be an RC-type filter. The first filter 208 may remove a degree of relatively high-frequency noise (for example, switching noise). The output of the first filter 208 may be provided to APD circuitry 210. The filtered voltage from the first filter 208 may be used to reverse-bias the APD, which may be included in the APD circuitry 210. The APD may include a Hamamatsu S8664 series APD.

A second filter 212 may also be provided as part of the output filter network to the switching power supply. Altogether, the output filter network may include an RC-type filter (an example of the first filter 208) followed by the APD circuitry 210, and an additional output capacitor used to provide additional device stabilization (an example of the second filter 212). Because the impedance of the APD mimics that of a capacitor, it may be built into the output filter network and act as a component in the device output filter circuitry. The output filter circuitry may use relatively large values that are typically too large for commercially-practical power supply circuits. However, because the APD requires relatively low bias currents, the output filter network can use these otherwise impractical components to aid in achieving advantageously low noise levels. For example, output voltage noise measured in a 20 MHz bandwidth has been shown to be below 150 microvolts (VRMS).

The APD circuitry 210 may output a current signal when it receives light in a given frequency range. The current signal may be converted and/or amplifiers by one or more amplifiers. The amplifier(s) may include a first amplifier 216 and optionally a second amplifier 218. The first amplifier 216 may convert the current signal to a voltage signal. The second amplifier 218 may provide additional gain if/as needed by amplifying the output provided by the first amplifier 216. The second amplifier 218 may also invert the signal to mimic a PMT voltage output signal. Although not shown, the output of the second amplifier may be a voltage signal which may be digitized (for example, by A-to-D converter 230) and communicated to a processor (such as processor 222). A different processor (not shown) and/or another A-to-D converter (not shown) may be used for digitization/processing of the output signal. In addition to the feedback loop in the power supply, a second feedback loop may be included in the circuitry represented by block diagram 200. This second feedback loop may include voltage adjustment circuitry, which is configured to adjust a voltage on the first feedback loop based at least in part on a voltage measured between the first filter 208 and the APD circuitry 210. This second feedback loop (including the voltage adjustment circuitry) may include read back circuitry 228, multiplexer 226, A-to-D converter 230, processor 222, D-to-A converter 224, and circuitry 220. The second feedback loop may influence the voltage at the feedback node in the DC boost switching power supply to adjust its output based potentially a variety of factors, including the substantially real-time voltage at or proximate the APD. The particular techniques disclosed for the second feedback loop including voltage adjustment circuitry are just one of many different possible techniques that can influence the voltage at the feedback node of the power supply according to a voltage measured between the first filter 208 and the APD circuitry 210.

The read back circuitry 228 may receive the voltage between the first filter 208 and APD circuitry 210. The read back circuitry 228 may include an amplifier to amplify the received voltage. The output of the readback circuitry 228 may be provided to multiplexer 226. The multiplexer 226 may be an analog multiplexer, and it may receive a plurality of input signals. Such signals may include the output of the readback circuitry 228, the output of a temperature sensor amplifier 232, and/or the output of the amplifier network that conditions the output signal from the APD circuitry 210 (not shown). The processor 222 may provide a select signal to the multiplexer 226 to determine which of these (or other) signals will be output from the multiplexer 226. The output of the multiplexer 226 is provided to the A-to-D converter 230 (for example, 16-bit). The digitized output of the A-to-D converter 230 may be provided to the processor 222. Thus, the digital signal encodes the measured voltage between the first filter 208 and the APD circuitry 210.

The processor 222 may execute an equation or algorithm (through processing) to generate a digital output signal. The equation or algorithm may account for different input variables, including the voltage between the first filter 208 and the APD circuitry 210, the temperature at or near the APD, and/or APD device characteristics (for example, APD reverse voltage VR or breakdown voltage VBR). The output signal from the processor may be provided to the D-to-A converter 224 (for example, 16-bit), and the analog output (an adjustment voltage) of the converter 224 may be received by circuitry 220. Circuitry 220 may condition the signal (for example, filter/amplify the output of the converter 224). The output of the circuitry 220 may influence or cause the voltage at the feedback input (or node) to the high-voltage generator circuitry 204 to change. The feedback node voltage is influenced by the electrical signal summation of the digital-to-analog converter 224 voltage output and the output voltage of the DC-DC converter. The feedback voltage generated from the output of the DC-DC converter combines with the digital-to-analog converter 224 output to generate the power supply output voltage.

The temperature sensor 234 (for example a TI LM35 series sensor) may provide a temperature reading with a minimum of 0.25° C. linearity. The temperature sensor 234 output may be amplified by temperature sensor amplifier 232 before it is provided to multiplexer 226. The temperature may be measured at periodic intervals for changes from when the last user adjustment from an operator occurred. Based on the change in temperature, the processor 222 may either increase or decrease the APD reverse-bias voltage. A slope calculation from the configuration step of the APD may be used to adjust the voltage bias by a fixed amount for every 0.25° C. change at the temperature sensor (near or at the APD).

For example, each 0.25° C. temperature change may be converted into a number of digital counts based on the slope of the output voltage. It is then determined how many digital counts are needed need to generate 'X' voltage value. The slope value is generated for each power supply by setting the power supply's digital-to-analog converter 224, measuring the output voltage of the power supply, setting the digital-to-analog converter 224 to a different value, and measuring the output voltage. This results in an equation: (voltage2−voltage1)/(DAC_value2−DAC_value1)=slope. The slope informs how much voltage the output will change per digital-to-analog converter 224 count value. It may be known that for every single degree C. change, the device will need to adjust by, for example, 0.78V. So for every 0.25° C., it may be known that the output will need to be adjusted by 0.78V/4, or 0.195V at the output. The slope determines how many digital counts are needed to effect the proper change (either up or down depending on if temperature is increasing or decreasing). For example, if the slope is 0.0076, and the temperature changes by 0.25° C., the digital-to-analog converter 224 may need to be adjusted by 0.195V/0.0076, which equals 26 digital counts.

Consider the following illustrative example for the operation of circuitry illustrated by block diagram 200.

Each APD may have a different operating voltage bias and breakdown voltage. The APD reverse voltage (VR) and breakdown voltage (VBR) may be specified by the APD manufacturer. These characteristics of a particular APD may be stored in memory (for example, non-volatile memory) readable by the processor (for example, integrated EEPROM). Thus, each cytometer may be individualized for a given APD. Supply output voltage values may also be measured (for example, using an external NIST traceable voltmeter) as part of a one-time configuration process for each cytometer, and these calibration values for the output voltage may then be stored in memory (along with the other unique variables for the APD as discussed above).

For each given system, the VREF value may control the APD's voltage bias. For example, a value of 0.5V at VREF may correspond to an optical gain of M=50 for the APD and moving the value from 0.1V to 1V may adjust the gain of the APD by increasing the bias voltage. Protection algorithms may be built into the processor 222 such that an unreasonably high VREF may not allow the APD to reach breakdown voltage, and therefore the APD may be protected. Under certain conditions, because VREF adjusts the optical gain at the APD, this does not mean that the supply simply adjusts the output voltage in the same increments for each device for a given VREF. This is because from VREF=0.1 to 1V, the algorithm used to control the flyback converter supply may treat the VREF signal as an optical gain parameter, and not a voltage adjustment parameter. This may mean that a VREF of 0.5V may produce a different voltage value which is unique for the given APD installed in the system. If an APD has a VR of 403.3V for M=50, and a separate APD has a VR value of 390.8V for M=50, the VREF input of 0.5V may still be selected to produce the exact same optical gain of M=50.

This means that the output voltage adjustment through VREF may actually be a function of the desired optical gain, which may be unique to the APD device itself, and is not a uniformly applicable output voltage adjustment. These customized values corresponding to the characteristics may be programmed into each system at startup, and the customized characteristics may enable uniform "black box" performance across all similarly configured systems. Because the flyback power supply may utilize a hybrid analog and digital feedback from different nodes, the output voltage to achieve the M=50 may be obtained by comparing the high voltage readback signal of the actual APD itself, and the processor 222 may generate an error term from the flyback's analog control generated value. The second feedback loop value may be converted into a digital count based on the slope of a linear curve fit performed at the initial startup configuration. When a user sets VREF at ostensibly 0.5V, the processor 222 may recognize that based on the values entered, the particular APD installed needs a reverse-bias voltage of 403.3V, and sets the precise VREF to be something potentially different from 0.5V.

The digital-to-analog converter 224 may be sent a value determined from the initial configuration at startup, and, if the APD was not present in the output filter, it may have the correct output voltage. However, because the first filter 208 may use relatively large value resistor component(s), the feedback network of the supply may "think" it is providing the correct voltage when really it is offset because the system now has an APD present in the output filter network. The second feedback node, which may be a digitized value of the actual output voltage at or proximate the APD (for example, a voltage at a location between the first filter 208 and the APD circuitry 210), may then be used to solve an internal slope compensation equation (or other suitable algorithm) in the processor 222 that sets the correct output voltage for a desired optical gain. This algorithm may then be used to adjust the D-to-A converter 224 value sent to the flyback converter's feedback node.

Temperature compensation may also be implemented. Once the optical gain is set for M=50, the processor may measure the temperature, and for example, for any changes in 0.5° C. (or other suitable increment), the output voltage that was used for M=50 may be adjusted to a new value, for example, based on the breakdown coefficient of the APD to keep the gain set at M=50. This means that temperature compensation may be invoked after an interval of time has passed since VREF has changed. This may allow for temperature once a user has set VREF (because not all systems will want M=50, some may be at M=55, M=60, or other suitable optical gains depending on the desired mode of operation).

Figure 3:
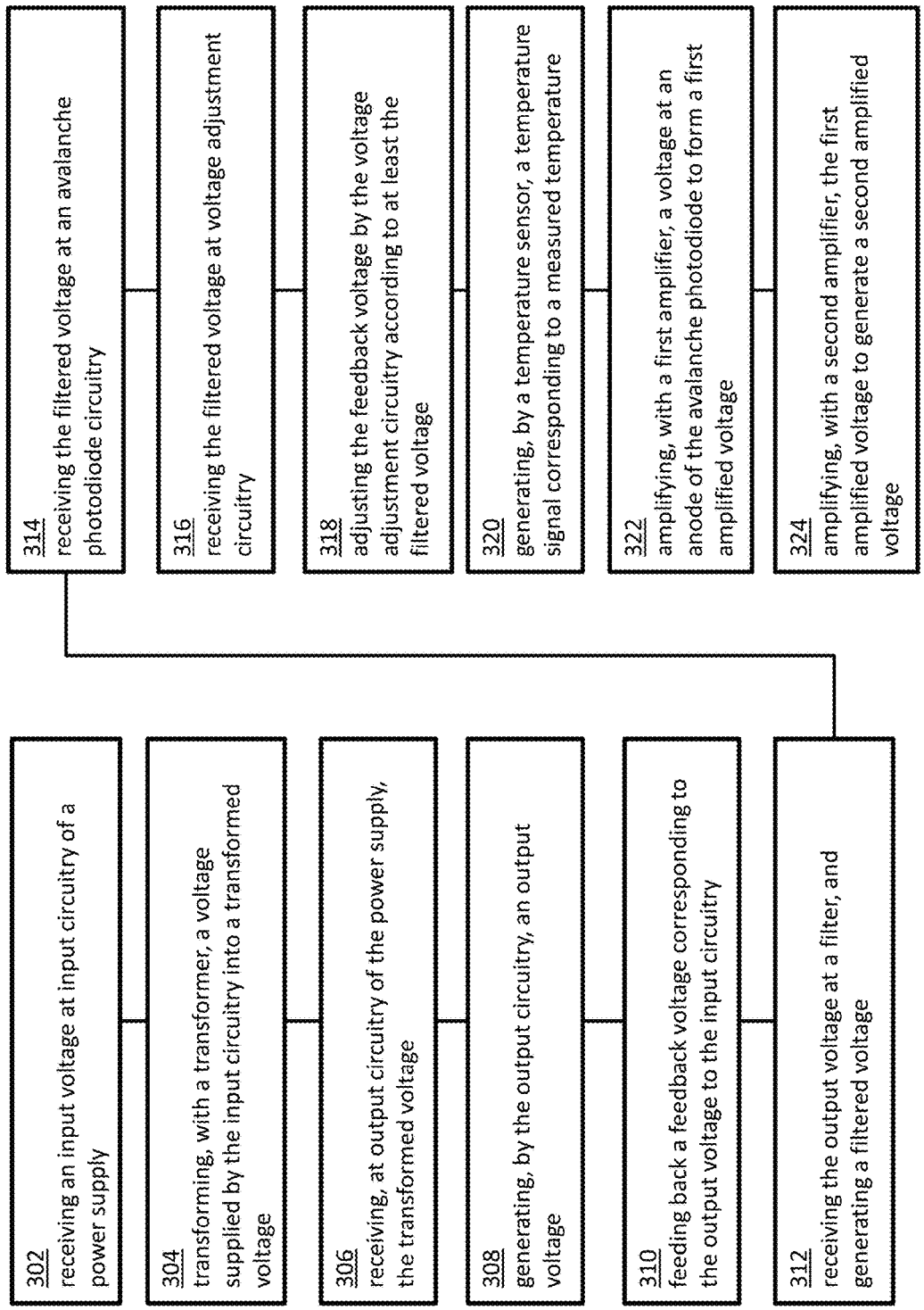
FIG. 3 illustrates a flowchart for a method, according to certain inventive techniques.

FIG. 3 illustrates a flowchart 300 for a method, according to certain inventive techniques. The method may be performed by systems 100 or 200. The certain steps in the flowchart 300 may be performed at times overlapping other steps or substantially simultaneously with other steps. Certain steps could be performed in a different order, and there is no implication by the flow of flowchart 300 that steps must be performed in any particular order.

At step 302, an input voltage may be received at input circuitry (for example, high-voltage generator circuitry 204) of a power supply, such as a DC/DC boost switching power supply. At step 304, a transformer (for example, transformer 206) transforms a voltage supplied by the input circuitry into a transformed voltage. At step 306, output circuitry (for example, one or more Schottky diodes in series between the transformer 206 and the first filter 208) of the power supply receives the transformed voltage. At step 308, the output circuitry generates an output voltage. At step 310, a voltage corresponding to the output voltage is fed back to the input circuitry. At step 312, the output voltage is received at a filter (for example, first filter 208), and a filtered voltage is generated by the filter. At step 314, the filtered voltage is received at APD circuitry (for example, APD circuitry 210), which includes an APD. At step 316, the filtered voltage is received at voltage adjustment circuitry (for example, read back circuitry 228). This circuitry may be part of the second feedback loop, as discussed above. At step 318, the feedback voltage may be adjusted by the voltage adjustment circuitry according to at least the output voltage.

At step 320, a temperature sensor (for example, temperature sensor 234) may generate a temperature signal corresponding to a measured temperature (that is, a sensed temperature). Furthermore, step 318 may further include adjusting the feedback voltage by the voltage adjustment circuitry according to at least the filtered voltage and the measured temperature. Additionally, step 318 may further adjusting the feedback voltage by the voltage adjustment circuitry according to at least the filtered voltage, the measured temperature, and at least one value corresponding to a characteristic of the avalanche photodiode. Also, step 318 may further include adjusting the feedback voltage by the voltage adjustment circuitry according to at least the filtered voltage and at least one value corresponding to a characteristic of the avalanche photodiode.

According to one technique, step 318 further includes: converting, with an analog-to-digital converter (for example, analog-to-digital converter 230), the filtered voltage into a digital measured signal encoding filtered voltage data; processing, with a processor (for example, processor 222), at least the filtered voltage data to generate a digital adjustment signal; converting, by a digital-to-analog converter (for example, digital-to-analog converter 224), the digital adjustment signal to an adjustment voltage; and adjusting the feedback voltage according to the adjustment voltage. According to another technique, said processing at least the output voltage data may further include processing at least temperature data and the filtered voltage data to generate the digital adjustment signal. According to another technique, said processing at least the output voltage data further comprises processing at least data corresponding to at least one characteristic of the avalanche photodiode, temperature data, and the filtered voltage data to generate the digital adjustment signal. According to another technique, the at least one characteristic of the avalanche photodiode comprises at least one of a breakdown voltage and a reverse bias voltage corresponding to a predetermined optical gain.

At step 322, a first amplifier (for example, first amplifier 216) may amplify a voltage at an anode of the avalanche photodiode to form a first amplified voltage. At step 324, a second amplifier (for example, second amplifier 218) may amplify the first amplified voltage to generate a second amplified voltage.

Figure 4:
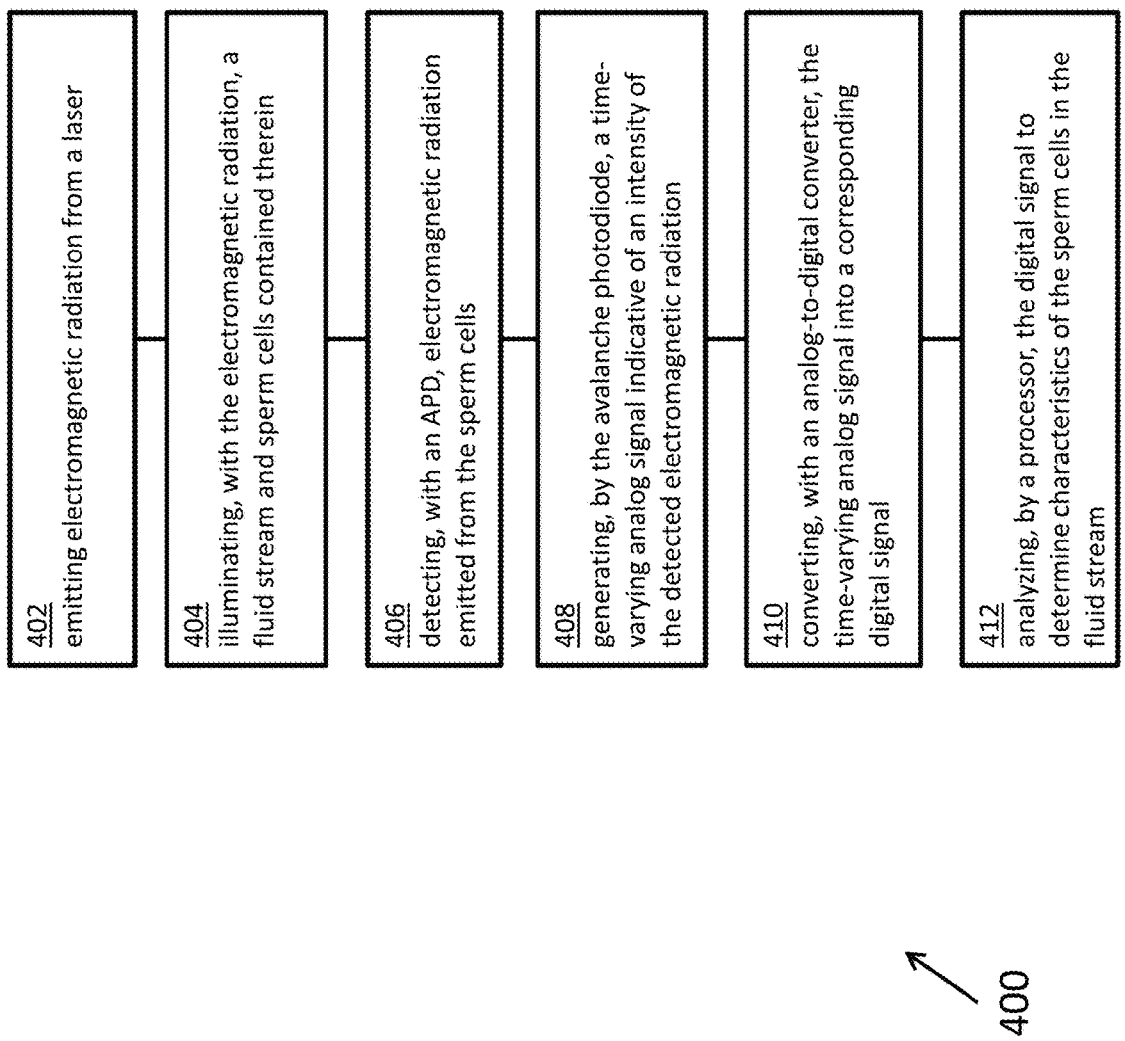
FIG. 4 illustrates a flowchart for a method, according to certain inventive techniques.

FIG. 4 illustrates a flowchart 400 for a method, according to certain inventive techniques. The method may be performed by systems 100 or 200. The certain steps in the flowchart 400 may be performed at times overlapping other steps or substantially simultaneously with other steps. Certain steps could be performed in a different order, and there is no implication by the flow of flowchart 400 that steps must be performed in any particular order.

At step 402, electromagnetic radiation (for example, light of a given wavelength) is emitted from a laser (for example, laser 106). At step 404, a fluid stream and sperm cells contained therein are illuminated with the electromagnetic radiation. At step 406, an APD (for example, photodetector 112) detects electromagnetic radiation emitted from the sperm cells. This emitted radiation (for example, light of a given wavelength) may be generated by a fluorescing dye (for example, stained on sperm chromosomes) that generates responsive radiation in response to received radiation. At step 408, the APD generates a time-varying analog signal indicative of an intensity of the detected electromagnetic radiation. At step 410, an analog-to-digital converter (for example, converter 230) converts the time-varying analog signal into a corresponding digital signal. The time-varying signal may be processed before digitization (for example, by readback circuitry 228). At step 412, a processor (for example, processor 222) analyzes the digital signal to determine characteristics of the sperm cells in the fluid stream.

Figure 5:
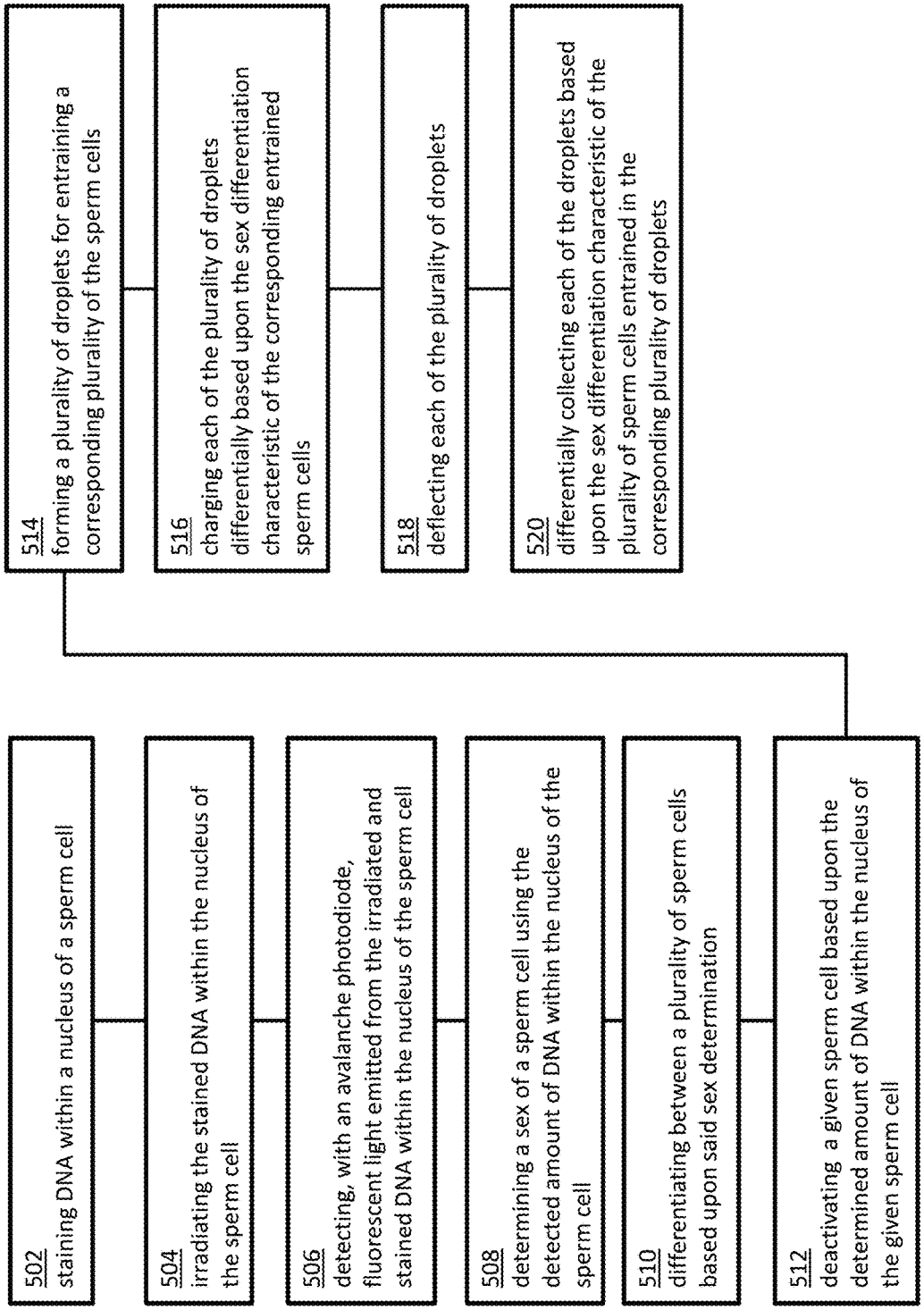
FIG. 5 illustrates a flowchart for a method, according to certain inventive techniques.

FIG. 5 illustrates a flowchart 500 for a method, according to certain inventive techniques. The method may be performed by systems 100 or 200. The certain steps in the flowchart 500 may be performed at times overlapping other steps or substantially simultaneously with other steps. Certain steps could be performed in a different order, and there is no implication by the flow of flowchart 500 that steps must be performed in any particular order.

At step 502, DNA within a nucleus of a sperm cell (for example, sperm cell 104) is stained, for example, with a DNA-intercalating, fluorescing dye. At step 504, the stained DNA within the nucleus of the sperm cell is irradiated (for example, by laser 106). At step 506, fluorescent light emitted from the irradiated and stained DNA within the nucleus of the sperm cell is detected with an avalanche photodiode (for example, photodetector 112).

At step 508, a sex of a sperm cell is determined using the detected amount of DNA within the nucleus of the sperm cell. For example, a sperm cell with XX chromosomes may have 3% more DNA than a sperm cell with XY chromosomes. This may lead to a corresponding increase (linear or non-linear increase) of light emission from the stained DNA. Due to the inventive techniques disclosed herein, it may be possible to measure this difference with an avalanche photodiode, thereby determining the "sex" of a sperm cell. At step 510, a plurality of sperm cells are differentiated based upon said sex determination. The cells may be sorted (creating two or more populations; for example, an X-chromosome population and a non-X-chromosome population), or cells within the population can be selected for deactivation (for example, by laser ablation).

At step 512, a given sperm cell may be deactivated based upon the determined amount of DNA within the nucleus of the given sperm cell. For example, processor 114 may control operation of kill/segregation componentry 118 to deactivate (separate, degrade, or destroy) the sperm cell so it may not be useful for fertilization based on the result of step 510. One technique of deactivation is illustrated generally by steps 514, 516, 518, and 520. At step 514, a plurality of droplets may be formed for entraining a corresponding plurality of the sperm cells. At step 516, each of the plurality of droplets may be differentially charged based upon the sex differentiation characteristic of the corresponding entrained sperm cells. At step 518, each of the plurality of droplets may be deflected. At step 520, each of the droplets may be differentially collected based upon the sex differentiation characteristic of the plurality of sperm cells entrained in the corresponding plurality of droplets.

For example, one approach for sexing is laser-kill in which anything that is not an X-chromosome-bearing sperm cell may be ablated via laser pulse. Such techniques are described in U.S. Pat. Nos. 8,933,395, 9,000,357, 9,140,690, and 9,335,295, the entireties of which are herein incorporated by reference.

As another example, charge/deflection techniques are also used in the sexing industry. Such techniques are described in U.S. Pat. No. 9,145,590, the entirety of which is herein incorporated by reference. Other conceivable approaches include the use of optical traps and/or laser steering, as described in U.S. Pat. Nos. 8,149,416 and 8,158,927, the entireties of which are herein incorporated by reference.

It will be understood by those skilled in the art that various changes may be made and equivalents may be substituted without departing from the scope of the novel techniques disclosed in this application. In addition, many modifications may be made to adapt a particular situation or material to the teachings of the novel techniques without departing from its scope. Therefore, it is intended that the novel techniques not be limited to the particular techniques disclosed, but that they will include all techniques falling within the scope of the appended claims.

What is claimed is:

1. A method for assessing an amount of DNA within a nucleus of a sperm cell comprising:
   staining the DNA within the nucleus of the sperm cell;
   irradiating the stained DNA within the nucleus of the sperm cell; and
   detecting, with at least one avalanche photodiode, fluorescent light emitted from the irradiated and stained DNA within the nucleus of the sperm cell.

2. The method of claim 1, further comprising:
   determining a sex of a sperm cell using the detected fluorescent light within the nucleus of the sperm cell; and
   differentiating between a plurality of sperm cells based upon said sex determination.

3. The method of claim 2, further comprising forming droplets, a plurality having one of said sperm cells entrained.

4. The method of claim 3, further comprising charging each of said droplets differentially based upon said sex differentiation characteristic of said sperm cells entrained in said droplets.

5. The method of claim 4, further comprising deflecting each of said droplets.

6. The method of claim 5, further comprising differentially collecting each of said droplets based upon said sex differentiation characteristic of said sperm cells entrained in said droplets.

7. A population of sperm cells comprising the droplets produced by the method of any of claims 3-6.

8. The method of claim 2, further comprising deactivating a sperm cell based upon the determined amount of DNA within the nucleus of said sperm cell.

9. The method of claim 8, further comprising photo-damaging said sperm cell.

10. The method of claim 9, further comprising forming droplets a plurality having one of said sperm cells entrained.

11. The method of claim 10, further comprising charging each of said droplets differentially based upon said sex differentiation characteristic of said sperm cells entrained in said droplets.

12. The method of claim 11, further comprising deflecting each of said droplets.

13. The method of claim 12, further comprising differentially collecting each of said droplets based upon said sex differentiation characteristic of said sperm cells entrained in said droplets.

14. A high-purity population of sperm cells comprising the droplets produced by the method of any of claims 10-13.

* * * * *